US012678190B2

(12) United States Patent
Norman et al.

(10) Patent No.: US 12,678,190 B2
(45) Date of Patent: *Jul. 14, 2026

(54) SURGICAL KIT FOR MINIMALLY INVASIVE SPINE SURGERY

(71) Applicant: Intersect ENT International GmbH, Hennigsdorf (DE)

(72) Inventors: Nicholas Norman, Charlotte, NC (US); Robert Hedermann, Berlin (DE); Malte Bergfeld, Berlin (DE); Dirk Mucha, Glienicke/Nordbahn (DE); Kai Desinger, Berlin (DE)

(73) Assignee: Fiagon GMBH, Hennigsdorf (DE)

( * ) Notice: Subject to any disclaimer, the term of this patent is extended or adjusted under 35 U.S.C. 154(b) by 1011 days.

This patent is subject to a terminal disclaimer.

(21) Appl. No.: 17/516,590

(22) Filed: Nov. 1, 2021

(65) Prior Publication Data

US 2022/0047295 A1 Feb. 17, 2022

Related U.S. Application Data

(63) Continuation of application No. PCT/EP2020/062349, filed on May 4, 2020.

(Continued)

(51) Int. Cl.
*A61B 17/34* (2006.01)
*A61B 1/018* (2006.01)
(Continued)

(52) U.S. Cl.
CPC .......... *A61B 17/3403* (2013.01); *A61B 1/018* (2013.01); *A61B 17/1757* (2013.01);
(Continued)

(58) Field of Classification Search
CPC ..... A61B 17/34; A61B 17/3403; A61B 17/17; A61B 17/1757; A61B 1/018; A61B 34/10; A61B 34/20
See application file for complete search history.

(56) References Cited

U.S. PATENT DOCUMENTS 6,161,032 A * 12/2000 Acker .................... A61B 5/062
324/207.11
9,471,850 B2 10/2016 Krueger et al.
(Continued)

FOREIGN PATENT DOCUMENTS

DE 102011119073 A1 5/2013
EP 0691663 A1 1/1996
(Continued)

OTHER PUBLICATIONS

European Patent Office, International Search Report and Written Opinion for PCT/EP2020/062086, Aug. 7, 2020, 10 pages.
(Continued)

*Primary Examiner* — Christopher J Beccia
(74) *Attorney, Agent, or Firm* — Nancy C. Wilker

(57) ABSTRACT

The invention relates to a surgical kit, for performing minimally invasive spine surgery. The surgical kit comprises a position detection system, configured for detecting position and orientation of localizers from received sensor signals in the position detection system's coordinate system. The surgical kit also comprises a sensor carrier, configured to be removably arranged in a lumen of a medical instrument, the sensor carrier having at least two localizers, the localizers each being configured for providing a sensor signal representing position and orientation of the respective localizer. Furthermore, the surgical kit comprises a plurality of medical instruments having a lumen in which the sensor carrier can be removably arranged for connecting the respective medical instrument to the position detection system.

14 Claims, 8 Drawing Sheets

Related U.S. Application Data

(60) Provisional application No. 62/915,197, filed on Oct. 15, 2019, provisional application No. 62/888,631, filed on Aug. 19, 2019, provisional application No. 62/844,922, filed on May 8, 2019, provisional application No. 62/842,025, filed on May 2, 2019.

(51) Int. Cl.

| | |
|---|---|
| *A61B 17/17* | (2006.01) |
| *A61B 34/10* | (2016.01) |
| *A61B 34/20* | (2016.01) |
| *A61B 17/00* | (2006.01) |

(52) U.S. Cl.
CPC .............. *A61B 34/10* (2016.02); *A61B 34/20* (2016.02); *A61B 2017/00022* (2013.01); *A61B 2017/00455* (2013.01); *A61B 2017/00725* (2013.01); *A61B 2034/102* (2016.02)

(56) References Cited

U.S. PATENT DOCUMENTS

| | | | |
|---|---|---|---|
| 10,022,525 | B2 | 7/2018 | Hanson et al. |
| 10,238,846 | B2 | 3/2019 | Ressemann et al. |
| 2003/0066538 | A1 | 4/2003 | Martinelli et al. |
| 2009/0234329 | A1 | 9/2009 | Inamoto et al. |
| 2010/0274188 | A1 | 10/2010 | Chang et al. |
| 2011/0066029 | A1 | 3/2011 | Lyu et al. |
| 2013/0102878 | A1* | 4/2013 | Burg ...................... A61B 5/062 600/411 |
| 2014/0303489 | A1* | 10/2014 | Meier .................. A61B 5/0002 600/424 |
| 2014/0317910 | A1 | 10/2014 | Govari et al. |
| 2016/0310041 | A1 | 10/2016 | Jenkins et al. |
| 2017/0028112 | A1 | 2/2017 | Drontle et al. |
| 2017/0196508 | A1* | 7/2017 | Hunter ................. A61B 5/4566 |
| 2018/0093087 | A1 | 4/2018 | Beach |
| 2018/0296811 | A1 | 10/2018 | Chan et al. |
| 2019/0015644 | A1 | 1/2019 | Thomspon Smith et al. |
| 2019/0038366 | A1 | 2/2019 | Johnson et al. |

FOREIGN PATENT DOCUMENTS

| | | |
|---|---|---|
| WO | WO-2012150567 A1 | 11/2012 |
| WO | WO-2020221885 A1 | 11/2020 |
| WO | WO-2020221940 A1 | 11/2020 |

OTHER PUBLICATIONS

European Patent Office, International Search Report and Written Opinion forPCT/EP2020/062349, Aug. 7, 2020, 13 pages.
The International Bureau of Wipo, International Preliminary Report onPatentability for PCT/EP2020/062086, Nov. 2, 2021, 7 pages.
The International Bureau of Wipo, International Preliminary Report onPatentability for PCT/EP2020/062349, Nov. 2, 2021, 9 pages.

\* cited by examiner

M1
M2
M3
M4
M5
M6
M7

M14
M13
M12
M11
M10
M9
M8

M15

M16

M17
M18
M19

SURGICAL KIT FOR MINIMALLY INVASIVE SPINE SURGERY

CROSS-REFERENCE TO RELATED APPLICATIONS

This application is a continuation of International Patent Application No. PCT/EP2020/062349 filed on May 4, 2020, which claims priority to U.S. Provisional Patent Application Nos. 62/915,197 filed on Oct. 15, 2019, 62/888,631 filed on Aug. 19, 2019, 62/844,922 filed on May 8, 2019, and 62/842,025 filed on May 2, 2019. Each of the foregoing disclosures is hereby incorporated by reference in its entirety.

TECHNICAL FIELD

The invention relates to a surgical kit for performing minimally invasive spine surgery. The invention also relates to a method for removing at least a part of an intervertebral disc and/or surrounding body tissue. The invention further relates to a method for fusing at least two vertebrae.

BACKGROUND OF THE INVENTION

For assisting a surgeon in using a medical instrument in a surgical procedure it is known to track the position of the medical instrument inside a patient's body and to display the medical instrument's position in, e.g., sectional images of a model of a patient on a monitor.

To this end, surgical navigation systems are used typically comprising a position detection system, a monitor, and one or more localizers. The position detection system can be, e.g., an optical position detection system, an ultrasound-based position detection system or an electromagnetic position detection system. A position detection system, in general, is configured for determining position and orientation of localizers. The localizers can be mounted on a medical instrument to allow tracking of the medical instrument by means of the position detection system.

By way of example, electromagnetic position detection systems are known having a field generator for generating an alternating electromagnetic field. A medical instrument to be used with an electromagnetic position detection system is equipped with a localizer that typically comprises one or more sensor coils.

When exposed to an alternating electromagnetic field, in the sensor coils of a localizer a voltage is induced that depends on the position and orientation of a respective sensor coil in the alternating electromagnetic field. With a position detection system, a sensor signal representing the induced voltage can be tapped from the sensor coils and analysed for determining position and orientation of the localizer. Typically, position and orientation of a localizer of a medical instrument are determined relative to the position and orientation of a reference localizer, sometimes called patient localizer, that can likewise comprise sensor coils and that stays fixed relative to a patient.

In order to calculate position and orientation of the medical instrument equipped with a localizer relative to a position detection system, often, it is required to calibrate the position of the medical instrument's tip to the position of the localizer. To this end, typically a calibration device is employed that has known position and orientation relative to the position detection system. For example, the calibration device can likewise be equipped with a localizer the position and orientation of which can be determined with the position detection system. By means of calibration, a transformation function, sometimes called calibration matrix, can be established representing the spatial relationship between the position and orientation of a medical instrument's localizer and the medical instrument's tip. The established transformation function can be used during a navigated procedure for displaying the position of the medical instrument's tip in sectional images of a patient's model on a monitor.

For displaying the medical instrument's position in sectional images of a patient's model on a monitor of a navigation system, it is typically further required to register the patient model to the patient. Often, a model of a patient is a topographic image that is generated from two-, three- or four-dimensional images of a patient obtained preoperatively by tomography, e.g., via computed tomography (CT), magnetic resonance imaging (MRI) or C-arm fluoroscopic imaging. Registration refers to obtaining the spatial correlation between position and orientation of a patient in real space (sometimes also called patient space) and the patient model, initially defined in terms of coordinates in the coordinate system of the respective two-, three- or four-dimensional image used for generating the patient model.

Having calibrated the medical instrument and having registered the patient model, the position of a medical instrument can be displayed in sectional images of the patient model for visually assisting a surgeon in navigating the medical instrument.

SUMMARY OF THE INVENTION

It is an object of the invention to provide an improved surgical kit for performing minimally invasive spine surgery. It is also an object of the invention to provide an improved method for treating a herniated disc. It is a further object of the invention to provide an improved method for spinal fusion.

According to the invention a surgical kit for performing minimally invasive spine surgery is proposed, the surgical kit comprising a position detection system, a sensor carrier, and a plurality of medical instruments that differ from one another and that each have a lumen in which the sensor carrier can be removably arranged for connecting the respective medical instrument to the position detection system.

The surgical kit's sensor carrier is configured to be removably arranged in the lumen of a medical instrument of the plurality of medical instruments. The sensor carrier has at least two localizers the position and orientation of which can be determined with the position detection system. The sensor carrier's localizers each are configured for providing a sensor signal representing position and orientation of the respective localizer. A medical instrument being equipped with the sensor carrier can be connected to the position detection system. With the sensor carrier being arranged in a medical instrument's lumen, position and orientation of the sensor carrier's localizers can be determined by the position detection system from provided sensor signals. From determined position and orientation of the sensor carrier's localizers, position and orientation of the medical instrument can be calculated by the position detection system.

Preferably, a first one of the sensor carrier's localizers is arranged at or at least close to the distal end of the sensor carrier, i.e., at a distance of 5 mm or less from the sensor carrier's distal end. A second one of the localizers is arranged at a distance from the first localizer towards the proximal end of the sensor carrier.

Preferably, the at least two localizers are arranged within a distal end region of the sensor carrier, the distal end region extending from the sensor carrier's distal end up to the proximal end of that localizer of the at least two localizers, that is arranged closer towards the sensor carrier's proximal end. In other words, the distal end region preferably comprises that section of the sensor carrier that extends between the sensor carrier's distal end and the proximal end of that localizer of the at least two localizers that is arranged closer to the proximal end.

Preferably, at least the sensor carrier's first localizer and a second localizer, each are configured to act as a 5 DOF (degrees of freedom) sensor. Preferably, also in combination, the at least two localizers are configured to act as 5 DOF sensors. A 5 DOF senor can be realized by employing one or more sensor coils.

Position and orientation of a localizers comprising one or more sensor coils can be determined with an electromagnetic position detection system having a field generator for generating an alternating electromagnetic field. If a localizer comprises one or more sensor coils that are exposed to an alternating electromagnetic field, a sensor signal can be tapped from each of the sensor coils, the sensor signal representing position and orientation of the respective sensor coil in an electromagnetic field. The tapped sensor signal can be transmitted via a wired connection or via a wireless connection to the position detection system.

The surgical kit's position detection system is configured for detecting position and orientation of localizers from received sensor signals in the position detection system's coordinate system. Preferably, the surgical kit's position detection system is an electromagnetic position detection system comprising a field generator for generating an alternating electromagnetic field and further comprising a signal processing unit for processing sensor signals. Position and orientation of the at least two localizers each having one or more sensor coils can be determined in the alternating electromagnetic field from tapped sensor signals representing voltages induced in the sensor coils by the electromagnetic field. A position detection system's signal processing unit typically comprises an analog-to-digital converter and a digital signal processor.

For connecting a medical instrument to an electromagnetic position detection system, at least one of the sensor carrier's localizers, preferably, comprises at least one sensor coil. With one sensor coil only five degrees of freedom can be determined. The sixth degree, namely, the rotation around the longitudinal axis of the sensor coil, cannot be determined. A 6 DOF sensor can be implemented in that the sensor carrier's localizer comprises at least two sensor coils that are arranged at an angle, e.g., orthogonally, to each other. A 6 DOF sensor can also be implemented in that the sensor carrier has two localizers each having a sensor coil, wherein the sensor coils of the localizers are arranged such that their longitudinal axis enclose a non-zero angle, preferably an angle of 90°.

The sensor carrier can also comprise at least a third localizer that is configured for providing a sensor signal representing position and orientation of the third localizer. Preferably, the third localizer is arranged at a distance from the first and second localizers towards the sensor carrier's proximal end. Preferably, the third localizer is arranged at or at least close to the sensor carrier's proximal end.

The at least two localizers alone, or in combination with at least a third localizer can be used for bend detection. If the sensor carrier is inserted into the lumen of a rigid medical instrument and in the course of insertion, a change in the orientation and/or position of the localizers with respect to their relative positions to each other can be detected. The detected change can be used to determine a bend, i.e., an angle, in the medical instrument. Preferably, if a change in the orientation and/or position of the localizers is detected, e.g., with a position detection system, a warning signal is displayed on a monitor by means of the position detection system.

In particular, if the sensor carrier is arranged in a lumen of a medical instrument that has at least one angle along the length of its lumen, by means of determined position and orientation of the three localizers, it is possible to calculate the medical instrument's angle. Often, the determined angle is characteristic for a specific medical instrument and can be used for identifying the medical instrument with arranged sensor carrier with a medical instrument identification unit. For example, if the sensor carrier with at least three localizers is arranged in the lumen of an endoscope, preferably, the third localizer is located in an angled access port. Typically, the angle between access port and the rest of the endoscope is characteristic for the endoscope itself. From determined position and orientation of the third localizer and at least one of the at least two localizers, respectively, the endoscope's angle can be calculated by the position detection system and/or a calibration unit and used by a medical instrument identification unit for identifying the endoscope.

In case the sensor carrier comprises a third localizer, the third localizer, preferably, is arranged at or at least close to the sensor carrier's proximal end. In case the sensor carrier having a third sensor carrier arranged at or close to its proximal end, position and orientation of the third localizer, preferably, are used by a medical instrument identification unit for identifying the medical instrument and/or by the position detection system for calculating the sixth degree of freedom of the at least two localizers arranged within the medical instrument's distal end region. In case the localizers comprise sensor coils, calculating the sixth degree of freedom of the at least two localizers arranged within the medical instrument's distal end region can be achieved with the position detection system, in particular, when the third localizer's longitudinal axis has an angle to the longitudinal axis of at least one of the first and second localizers.

In order to be arranged in lumens of different medical instruments of the surgical kit that are used during a navigated procedure, the distance between the sensor carrier's proximal end and the distal end is preferably between 10 cm and 200 cm, in particular, between 15 cm and 150 cm, more preferably, between 20 cm and 100 cm. The outer diameter of the sensor carrier is preferably equal to or smaller than 3 mm, in particular, equal to or smaller than 1.5 mm, more preferably, equal to or smaller than 1 mm.

Preferably, the sensor carrier comprises a hypo tube extending from the distal end to the proximal end of the sensor carrier and enclosing the sensor carrier's at least two localizers. Preferably, a hypo tube enclosing the at least two localizers is configured to give mechanical stability to the sensor carrier and to protect the localizers from external influences.

Suitable materials of which the hypo tube of the sensor carrier can be made are for example polyurethane (PUR), polyethylene, silicone rubber or polyether ether ketone (PEEK), nitinol, nitinol alloy or stainless steel. Typically, a hypo tube is a long metal tube with micro-engineered features along its length that shall provide the desired mechanical properties of the hypo tube. The sensor carrier with a hypo tube made of one of these materials can advantageously be repeatedly sterilized and is biocompatible.

The sensor carrier can be used for connecting generally known medical instruments having a lumen, e.g., a lumen that originally was provided for a guidewire, to the position detection system. To this end, the sensor carrier is inserted into the medical instrument's lumen. With the arranged sensor carrier, the medical instrument can be connected to and used with the position detection system in a navigated procedure. In particular, during a navigated procedure, the position of the medical instrument relative to the position detection system can be calculated from determined position and orientation of the at least two localizers with the position detection system. A calculated position of a medical instrument can be displayed in sectional images of a patient model on a monitor connected to the position detection system for assisting a surgeon in guiding the medical instrument inside a patient's body. After having accomplished a navigated procedure, the sensor carrier can be removed from the medical instrument's lumen and the lumen can be used as a working channel for other medical instruments of the surgical kit, such as drills or forceps.

The surgical kit can comprise medical instruments that generally have a lumen in which the sensor carrier can be arranged for connecting the medical instrument to the position detection system, e.g., catheters, biopsy needles, access needles, and cannulated instruments, e.g., a Jamshidi needle, taps, screwdrivers and bone screws, e.g., pedicle screws, that can be placed with the screwdriver. Such medical instruments having the sensor carrier arranged in their respective lumen can be automatically identified using a medical instrument identification setup as described below.

Further medical instruments that can be part of the surgical kit and that can be equipped with the surgical kit's sensor carrier are medical instruments that commonly do not have a lumen, but that have been retrofitted with a lumen or that are manufactured with a lumen suitable for insertion of the sensor carrier ab initio. Such a medical instrument can be, e.g., a scalpel, a surgical saw, e.g. a bone saw, a bone file, a cautery, or forceps.

The at least two localizers arranged in the distal end region of the sensor carrier can be configured to implement and/or can be treated as one sensor or as independent sensors. In case of the sensor carrier being arranged in the medical instrument's lumen, the position of the first localizer and the position of the second localizer along the longitudinal axis of the medical instrument can be used by the position detection system to calculate one virtual longitudinal axis between the two localizers by drawing a virtual line connecting the two central positions of the localizers, for creating a comparatively stable and accurate virtual axis for the sensor carrier and medical instrument. A medical instrument's virtual longitudinal axis, preferably, is the axis that intersects the positions of the at least two localizers of the arranged sensor carrier. The medical instrument's virtual longitudinal axis is defined in the coordinate system of the position detection system based on position and/or orientation of localizers. The physical instrument axis is defined by means of coordinates in real space.

In case the sensor carrier is arranged in a lumen of a medical instrument it is an advantage that the medical instrument's virtual longitudinal axis can be determined by the position detection system and/or a calibration unit based on position and/or orientation of the sensor carrier's at least two localizers.

By using the positions of at least two localizers for determining a medical instrument's virtual longitudinal axis, it is possible to reduce an angle error resulting, inter alia, from a physical misalignment of the sensor carrier inside a medical instrument's lumen to less than one degree. Advantageously, this allows for maintaining a stable central axis, e.g., during a navigated procedure, also when the medical instrument is rotated.

In general, it is not required to use the orientations (but only the position) of the sensor carrier's at least two localizers for determining the medical instrument's virtual longitudinal axis. However, a calibration unit and/or the position detection system can be configured to also use the orientations of the at least two localizers for determining the virtual longitudinal axis in addition to or instead of the localizers' positions.

By means of position and/or orientation of the at least two localizers, a spatial relationship between a medical instrument's virtual longitudinal axis and the medical instrument's physical longitudinal axis can be determined by the position detection system and/or the calibration unit. Thereby it is possible to define and ensure the trueness of the medical instrument's virtual longitudinal axis to the medical instrument's physical longitudinal axis based on position and/or orientation of the localizers, respectively.

In the sensor carrier, the at least two localizers are preferably arranged at a distance from each other, said distance being chosen in dependence on the geometry of specific medical instruments of the surgical kit. Generally, a larger distance makes the determination of a medical instrument's virtual longitudinal axis more precise. Preferably, the distance between a sensor carrier's first localizer and a second localizer of the at least two localizers is between 25 cm and 5 cm, in particular, between 20 cm and 5 cm, even more preferably between 15 cm and 5 cm, e.g., 10 cm.

The surgical kit can comprise medical instruments having a lumen in which the sensor carrier can be arranged for connecting the medical instrument to a position detection system, e.g., catheters, access needles, taps, bone drill, balloon dilation devices, e.g., such balloon dilation devices that can be used for kyphoplasty, screwdrivers and bone screws, e.g., pedicle screws, that can be placed with the screwdriver.

The surgical kit's medical instruments can also comprise such medical instruments that commonly do not have a lumen, but that have been retrofitted with a lumen or that are manufactured with a lumen suitable for insertion of the sensor carrier ab initio. Such a medical instrument can be, e.g., a scalpel, a surgical saw, e.g. a bone saw, a bone file, a cautery, forceps, an endplate rasp, a cage trial device, or a cage placement device.

Advantageously, by means of the sensor carrier each of the medical instruments having a lumen can be connected to and used with the position detection system in order to determine the medical instrument's position and orientation relative to a patient. The position of the medical instrument, in particular, of the medical instrument's tip, can be displayed on a monitor for assisting surgeon in tracking the medical instrument inside a patient's body.

Preferably, one medical instrument of the plurality of medical instruments having a lumen is an access needle, having a lumen extending from the access needle's distal end to its proximal end. Preferably, the access needle is configured for being guided to a target location in a patient's body. An access needle can be a 18 G needle, a 20 G needle, or a pedicle access needle, e.g., a Jamshidi-needle.

Alternatively, or additionally to an access needle, the plurality of medical instruments having a lumen can comprise at least one of a guiding rod, having a lumen and being configured to be advanced over the guidewire, a working tube, configured to be advanced over at least one dilation tube and for providing a working channel for medical instruments, wherein at its distal end, the working tube is shaped such that it can be anchored to a patient's bone, a reamer, having a lumen in which an endoscope can be arranged and being configured to be arranged inside the working channel of the working tube for creating a posteriorlateral access to the central nervous system, or an endoscope, having at least one endoscope working channel for inserting another medical instrument, the endoscope being configured for medical imaging inside a patient's body.

Preferably, in addition to the endoscope working channel, the endoscope has at least one further lumen that can, e.g., be used for suction and irrigation purposes.

Preferably, in cross-section the dilation tube has eccentric shape. It is also possible to use several dilation tubes with increasing diameters for a step-by-step dilation of body tissue.

Preferably, at its distal end, the working tube has teeth for anchoring the working tube to a patient's bone.

Preferably, the endoscope is a video endoscope.

The guiding rod serves for guiding the working tube to a target location inside a patient's body.

In the lumens of each of the access needle, the guiding rod, the working tube, the reamer and the endoscope, the sensor carrier can be successively inserted for connecting the respective medical instrument to the position detection system. By means of detecting the position and orientation of the sensor carrier's localizers, it is possible to calculate the position of the medical instrument's tip with the position detection system and to display the tip position in sectional images of a patient on a monitor.

Preferably, a surgical kit comprising an access needle, a guiding rod, a working tube, a reamer and an endoscope further comprises a medical instrument, configured to be arranged inside the endoscope's working channel and for removing at least a part of an intervertebral disc and/or sur-rounding body tissue, at least one dilation tube, configured for being advanced over the guiding rod and for dilating an access path to a target location, and a guidewire, configured for being inserted into the access needle's lumen.

A surgical kit comprising an access needle, a guidewire, a guiding rod, at least one dilation tube, a working tube, a reamer, an endoscope, and a medical instrument that is configured to be arranged inside the endoscope's working channel and for removing at least a part of an intervertebral disc and/or surrounding body tissue, is particularly suitable for removing at least a part of an intervertebral disc and/or surrounding body tissue. Medical instruments, configured to be arranged inside the endoscope's working channel for removing at least a part of an intervertebral disc and/or surrounding body tissue comprise forceps in different sizes, punches in different sizes, knives, or bipolar devices, e.g., a set of forceps.

Alternatively, or additionally, the surgical kit's plurality of medical instruments having a lumen can also comprise at least one of a lamina screwdriver with lamina screw, the screwdriver having a lumen extending from a proximal end of the screwdriver to a distal end of the lamina screw, the screwdriver being configured for anchoring the lamina screw into a vertebra's lamina, a tap for tapping a hole into a vertebra for anchoring a bone screw, or a pedicle screwdriver with a pedicle screw, the screwdriver having a lumen extending from a proximal end of the screwdriver to a distal end of the pedicle screw, the screwdriver being configured for anchoring the pedicle screw into a vertebra's Pedicle.

The lamina screwdriver with lamina screw, the tap, and the pedicle screwdriver with a pedicle screw each have a lumen in which the sensor carrier can be removably arranged for connecting the respective medical instrument to the position detection system. In particular, the position of the lamina screw when placing the lamina screw, the position of the pedicle screw when placing the pedicle screw and the position of the tap when tapping a hole into a vertebra can be visualized in sectional images of the patient on a monitor to assist a surgeon in finding the right position for placing a bone screw or for correctly tapping a hole with the intended depth into the bone.

A surgical kit comprising a lamina screwdriver with lamina screw, a tap, and a pedicle screwdriver with a pedicle screw, preferably, further comprises at least one of an endplate rasp for the preparation of endplates of adjacent vertebrae for fitting a spine cage, a spine cage trial device, configured for allowing to test various spine cages in different sizes and to assess to the effect of a tested spine cage for restoring a disc space between adjacent vertebrae, a spine cage, configured for restoring disc space between two vertebrae when being arranged between the respective vertebrae.

For example, a spine cage trial device can be configured such that various spine cages each having a different dimension can be tested with the spine cage trial device for assisting a surgeon in finding that spine cage that suits for restoring disc space between adjacent vertebrae. Preferably, the spine cage trial device is configured such that a resulting disc space restoration of spine cage implantation can be previewed by a surgeon in order to find that spine cage that has the most suitable dimensions.

A surgical kit comprising an access needle, a lamina screwdriver with lamina screw, a tap, and a pedicle screwdriver, and a spine cage is particularly suitable for fusing at least two vertebrae. Preferably, the access needle has a lumen and is configured to be navigated to a patient's vertebra.

The surgical kit can comprise a medical instrument identification setup. The medical instrument identification setup comprises a sensor carrier equipped with at least localizers, a position detection system for determining position and orientation of the localizers, a calibration device serving as a calibration reference, a calibration unit for calibrating a surgical kit's medical instrument equipped with the sensor carrier, and a medical instrument identification unit for identifying the surgical kit's medical instrument.

The position detection system that is part of the surgical kit can also be the position detection system of the medical instrument identification setup. In particular, the sensor carrier that is part of the surgical kit can be the sensor carrier of the medical instrument identification setup. Preferably, the position detection system is connected to the calibration unit and/or the medical instrument identification unit.

The medical instrument identification setup is particularly suitable for identifying medical instruments of the surgical kit in the lumens of which the sensor carrier is arranged successively.

Preferably, for identifying a medical instrument of the surgical kit, a sensor carrier can be used that has a length that is equal to or smaller than the length of the lumen of that medical instrument of the surgical kit that has the shortest lumen. In this case, the sensor carrier can be arranged successively in each of the medical instrument's lumen with its full length. For each of the medical instruments of the surgical kit, the distance between the respective medical instrument's tip and the sensor carrier's localizers is unique and can be used for differentiating the medical instruments from others of the surgical kit. A distance calculated for one of the medical instruments can thus be used for identifying the medical instrument.

With respect to surgical kit it is an advantage of the medical instrument identification setup that the medical instrument identification setup facilitates a fast and easy switching between medical instruments of the kit. Further, in a surgical kit the medical instruments of the kit can be designed so as to be easily discriminated and thus reliably recognized.

For identifying a medical instrument of the surgical kit, it is also possible to use a sensor carrier that has a length that is larger than the lumens of at least two of the surgical kit's medical instrument's. In this case, identifying a medical instrument is possible, e.g., by means of the distance between the medical instrument's tip and at least one of the two localizers and, preferably, at least one of a medical instrument's angle or the length of that section of the sensor carrier that extends beyond the medical instrument's proximal end. For using the length of that section of the sensor carrier extends beyond the medical instrument's proximal end for identifying the medical instrument, in general, position and orientation of the medical instrument's proximal end as well as of the sensor carrier's proximal end have to be determined, e.g., with a position detection system. To this end, the sensor carrier can have a localizer arranged at the sensor carrier's distal end and another localizer arranged at a distance from the distal localizer towards the sensor carrier's proximal end.

In embodiments in which the surgical kit comprises a medical instrument identification setup, preferably, the calibration unit and/or the position detection system are configured for extrapolating a medical instrument's virtual longitudinal axis from the distal end of the arranged sensor carrier to thus determine the position of a distal end of a medical instrument in the lumen of which the sensor carrier is arranged. The calibration unit can be configured for calibrating a medical instrument using the position of a distal end of a medical instrument as determined via extrapolation. The position detection system can be configured for visualizing the position of a medical instrument's tip in sectional images on a monitor using the extrapolated position of the medical instrument.

A medical instrument's virtual longitudinal axis can also be calculated by a position detection system and displayed in sectional images of a patient model on a monitor to visualize position and orientation of the medical instrument with respect to patient's body part. The position detection system can be connected to the medical instrument identification unit to obtain which medical instrument has been identified. The position detection system can be configured for automatically adapting the settings for displaying a digital representation of the medical instrument on a connected monitor for the identified medical instrument.

Displaying a medical instrument's virtual longitudinal axis with respect to a patient's body part can be of particular relevance during a navigated procedure, e.g., when aiming at an anatomical target from a comparatively large distance, e.g., a distance of 5 cm to 15 cm, with a medical instrument, e.g., an access needle, with arranged sensor carrier.

The medical instrument identification setup's position detection system can be configured for comparing determined position and orientation of the at least two localizers and for determining distortions of a navigation field, e.g., of an electromagnetic field, based on the comparison. For example, electromagnetic field distortions can be caused by a metal object located close to the sensor coils of one of the localizers. Due to electromagnetic field distortions, position and orientation of a respective localizer cannot be determined correctly, thus, resulting in an incorrect calculation of the position of the medical instrument's tip by means of the position detection system. If electromagnetic field distortions are detected, the position detection system can be configured for performing a plausibility check for identifying a localizer the position and orientation of which can currently be reliably determined. For example, the position detection system can be configured for comparing the current position and orientation of a localizer with previously determined position and orientation of the localizer for checking whether position and orientation of this localizer can currently be reliably determined.

The medical instrument identification setup's calibration device is configured such that its position and orientation in the position detection system's coordinate system can be determined by the position detection system. For example, the calibration device can be arranged at a position whose coordinate is known in the position detection system's coordinate system. It is also possible that the calibration device likewise is equipped with at least one localizer that is configured to provide a sensor signal representing the localizer's position and orientation.

The calibration device can have different calibration regions that are advantageously designed for the calibration of different medical instruments, e.g., adapted to the medical instrument's geometries. Different calibration regions can be implemented by visual indicators on the calibration device. The calibration unit can be configured for detecting which of the different calibration regions has been contacted with a medical instrument's tip. The medical instrument identification unit can be configured for identifying a medical instrument based on which of the different calibration regions has been contacted with a medical instrument's tip.

Advantageously, with different calibration regions on the calibration device that, preferably, are visual indicators on the calibration device, it allows for automatically differentiating between two medical instruments, also in case the two respective medical instruments have the same working length.

The calibration unit can be configured to calculate a centering error and/or a positioning error and/or an angle error and to compensate for the calculated centering error and/or positioning error and/or angle error when calculating the distance between the calibration device and at least one of the two localizers.

The calibration device can be complemented by and thus be linked to a specific procedure and/or surgical workflow in the software of the medical instrument identification setup to enable automatic instrument identification by means of the procedure steps. If the calibration device is linked to a specific software workflow, a medical instrument can be calibrated on the calibration device for identifying the medical instrument and for displaying the corresponding visualization and/or workflow.

The linking of the calibration device to specific procedure and/or surgical workflow in the software can be implemented to enable automatically differentiating between two medical instruments that have the same working length. The software algorithm implementing the medical instrument identification can be configured for recognizing the possible medical instruments resulting from the calibration procedure and for proposing the medical instrument that is used in the current step of the workflow.

Preferably, the algorithm is configured to visualize all identified medical instruments which result from a calibration procedure and highlights that medical instrument which is proposed according to the predefined workflow for confirmation to a user. A user can choose for this medical instrument, but also for any other medical instrument in case the user did not follow the workflow.

Most preferred, the algorithm is configured to display the proposed medical instrument and other possible instruments for selection by a user for, e.g., a 3 second, 5 second or 10 second time duration, while, preferably, also displaying the remaining time, e.g., as a count down. The algorithm can be configured to automatically select the proposed medical instrument, if a user does not do any selection.

The medical instrument identification setup's calibration unit is configured for calibrating a medical instrument with the sensor carrier arranged in its lumen. Calibrating a medical instrument with the sensor carrier comprises calculating a distance between the medical instrument's tip and at least one of the two localizers based on the position and orientation of the calibration device and the position and orientation of at least one of the two localizers as determined by the position detection system. For example, for calibrating the medical instrument with the sensor carrier arranged in the medical instrument's lumen, the medical instrument's tip can be brought into contact with the calibration device.

The calibration unit can be configured for automatically detecting whether or not the medical instrument's tip is in contact with the calibration device by determining whether a virtual longitudinal axis defined by the positions of the at least two localizers intersects the known position of a calibration device over a predefined period of time and/or whether the distance between the calibration device and at least one of the localizers stays constant over a predefined period of time.

The calibration unit can be configured to start automatic calibration of the medical instrument when the medical instrument's tip is found to be in contact with the calibration device. In particular, when in contact, the distance between the calibration device and at least one of the two localizers can be determined which corresponds to the distance between the medical instrument's tip and the respective one of the at least two localizers.

By means of calibration, a transformation function can be established by the calibration unit, the transformation function representing the spatial relationship between the medical instrument's tip and the at least two localizers.

The medical instrument identification setup's medical instrument identification unit is configured for determining a length of the medical instrument's lumen at least from the calculated distance and for using the determined length of the lumen for identifying the medical instrument. In particular, the medical instrument identification unit is connected to the calibration unit for obtaining the calculated distance between the medical instrument's tip and the at least two localizers.

The invention includes the recognition that the length of a lumen of a medical instrument, typically, is characteristic for the medical instrument itself. Thus, a medical instrument can be identified by virtue of the length of its lumen.

The invention includes the further recognition that the length of a lumen of a medical instrument can be automatically obtained when calibrating the medical instrument with sensor carrier being arranged in the medical instrument's lumen. Thus, by means of the sensor carrier, the length of the medical instrument's lumen can automatically be determined and used for identifying the medical instrument.

Automatically obtaining the length of a medical instrument's lumen can be achieved with the medical instrument identification setup in that with the calibration unit the distance between the medical instrument's tip and at least one of the two localizers is calculated and in that the calculated distance is used by the medical instrument identification unit for determining the length of the medical instrument's lumen. The medical instrument identification unit is configured for automatically identifying the medical instrument based on the determined length of the lumen.

As a result, it is possible to automatically identify a calibrated medical instrument with arranged sensor carrier by means of the medical instrument identification setup's a medical instrument identification unit based on the length of the medical instrument's lumen.

The information of the identified medical instrument can be used, e.g., for adapting the way of displaying or visualizing the medical instrument on a monitor. For example, to visualize on a monitor a digital representation of that medical instrument that has been identified by a medical instrument identification unit, i.e., the medical instrument representation in 2D or 3D views can be specifically accurate to the identified medical instrument.

It is also possible to use information of the identified medical instrument for automatically adapting a workflow in software according to how the identified medical instrument is used in a navigated procedure.

It is also possible to use information of the identified medical instrument for automatically adapting the views on a monitor for the instrument that is being used. For example, if an endoscope is identified during a navigated procedure, the software can automatically switch to displaying the video view from the endoscope in parallel with navigation views. The medical instrument identification can also be linked to a defined software procedure workflow, where the combination of the medical instrument identification and software workflow can guide a surgeon through a navigated procedure.

Medical instruments of the surgical kit that can be identified with the medical instrument identification setup can comprise medical instruments that generally have a lumen in which the sensor carrier can be arranged for operatively connecting the medical instrument to a position detection system. Such medical instruments that generally have a lumen are, e.g., catheters, access needles, taps, screwdrivers and bone screws, e.g., pedicle screws, that can be placed with the screwdriver.

Further medical instruments of the surgical kit that can be equipped with the sensor carrier are such medical instruments that commonly do not have a lumen, but that have been retrofitted with a lumen or that are manufactured with a lumen suitable for insertion of the sensor carrier ab initio. Such a medical instrument can be a scalpel, a surgical saw, e.g. a bone saw, a bone file, a cautery, forceps, an endplate rasp, a cage trial device, or a cage placement device.

A medical instrument can be identified at least based on the distance between the medical instrument's tip and at least one of the two localizers which can be determined based on the position and orientation of the calibration device and the position and orientation of at least one of the two localizers. Additionally to the calculated distance, a medical instrument can be identified based on a calculated angle of a medical instrument and/or the length of that section of the sensor carrier that lies outside a medical instrument's lumen in which the sensor carrier is arranged, i.e., that part of the senor carrier that extends beyond the proximal end of the medical instrument's lumen.

By way of example, it is possible to automatically determine the length of the medical instrument's lumen based on the sensor carrier having a fixed length and the localizers of the sensor carrier being located at fixed relative positions, e.g., within a hypo tube. Preferably, the length of the sensor carrier is shorter than the length of the lumens of those medical instruments, that shall potentially be automatically identified during a navigated procedure. For example, the sensor carrier can have a length that corresponds to the length of the lumen of that medical instrument out of the plurality of medical instruments that shall be potentially be automatically identified that has the lumen with shortest length. Thus, when successively inserting the sensor carrier in each medical instrument of the plurality of medical instruments that shall potentially be automatically identified during a navigated procedure, for each of the medical instruments the distance between its tip and the localizers of the arranged sensor carrier is different compared to the distances obtained for other medical instruments out of the medical instruments of the surgical kit. For example, it is possible to first calculate the distance between a medical instrument's tip and at least one of the sensor carrier's localizers and to add the remaining length of the sensor carrier to the calculated distance in order to obtain the length of the medical instrument's lumen. For example, the value of the length of the sensor carrier can be provided a priori to a medical instrument identification setup's medical instrument identification unit and the medical instrument identification unit can be configured for using the provided sensor carrier length for determining the length of a medical instrument's lumen. In particular, if the position of a sensor carrier's localizer relative to the sensor carrier's distal end and/or proximal end is known, the distance from the localizer to the sensor carrier's distal end and/or proximal end, respectively, can be used by the medical instrument identification unit for determining the length of a medical instrument's lumen accommodating the sensor carrier.

If the sensor carrier is arranged in a medical instrument's lumen, the distance between the sensor carrier's localizers and the medical instrument's tip is characteristic for the length of the medical instrument's lumen. Therefore, from the calculated distance between localizers and the medical instrument's tip, the length of the lumen itself can be derived.

The surgical kit's sensor carrier can be provided with its longitudinal axis being pre-calibrated in the position detection system's coordinate system. A calibration matrix representing the spatial relationship can be used for calibrating and navigating a medical instrument having the sensor carrier arranged in its lumen.

In particular, if the medical instrument has a straight lumen, the sensor carrier's longitudinal axis matches the medical instrument's physical axis. The calibration matrix of the pre-calibrated medical instrument can advantageously be used by the position detection system and/or the calibration unit for calculating the medical instrument's virtual longitudinal axis and for extrapolating the medical instrument's distal end.

It is advantageous if the sensor carrier itself is rigid at least in that section in which the localizers are arranged such that the pre-calibrated state remains valid also outside the straight lumen of a medical instrument.

The calibration unit and the medical instrument identification unit can be components of data processing device, e.g., a computer, and can be implemented, e.g., by a processor, volatile and non-volatile computer memories and software.

The medical instrument identification unit can be configured for identifying a medical instrument with arranged sensor carrier by comparing a determined length of a lumen of the medical instrument with a plurality of lengths of different medical instruments comprised in a database. Preferably, the database contains the lengths of lumens at least of those medical instruments that are potentially being used during a navigated procedure. The database can be part of the medical instrument identification unit.

In some embodiments of the surgical kit, the at least two localizers are arranged at a distance to each other close to a distal end of the sensor carrier. The sensor carrier can comprise at least a third localizer that is configured for providing a sensor signal representing position and orientation of the third localizer. Preferably, the third localizer is arranged at a distance from the first and second localizers towards the sensor carrier's proximal end. Preferably, the third localizer is arranged close to the proximal end of the sensor carrier. A sensor carrier with a third localizer being arranged close to the proximal end of the sensor carrier is particularly suitable for determining an angle of a medical instrument. Like the length of a medical instrument's lumen, the angle of medical instrument can be used for identifying the medical instrument. For example, a sensor carrier with a third localizer can be arranged in the lumen of a medical instrument such that a medical instrument's angle is located between the at least two localizers and the third localizer. From determined position and orientation of the third localizer and at least one of the at least two localizers, respectively, the medical instrument's angle can be calculated and used by the medical instrument identification unit for identifying the medical instrument with arranged sensor carrier. Advantageously, position and orientation of at least one of the localizers arranged in the medical instrument's distal end region and position and orientation of the third localizer can also be used for determining the sensor carrier's rotational orientation around the medical instrument's longitudinal axis, i.e., around the medical instrument's physical axis.

With the surgical kit's medical instrument identification setup, it is possible to automatically identify a surgical kit's medical instrument by conducting the steps of providing a sensor carrier, configured to be removably arranged in a lumen of a medical instrument, the sensor carrier having at least two localizers, the localizers each being configured for providing a sensor signal representing position and orientation of the respective localizer, providing a calibration device, the position and orientation of which is known in the coordinate system of a position detection system, inserting the sensor carrier into a lumen of a medical instrument, determining position and orientation of the at least two localizers from provided sensor signals, calculating a distance between the calibration device and at least one of the two localizers based on the determined position and orientation of the at least two localizers to calibrate the medical instrument, determining the length of the medical instrument's lumen at least from the calculated distance, and using at least the determined length of the lumen for identifying the medical instrument.

Preferably, after insertion, the sensor carrier is arranged in the medical instrument's lumen such that the at least two localizers are arranged at a distance to each other along the longitudinal axis of the medical instrument.

In some variants the medical instrument identification method comprises the step of contacting a calibration device with a tip of the medical instrument.

It is particularly preferred that a distance between the calibration device and at least one of the two localizers is calculated based on position and orientation of at least one of the two localizers determined when the medical instrument's tip is in contact with the calibration device.

If the calibration device likewise is equipped with at least one localizer, position and orientation of the calibration device's localizer can also be determined with a position detection system in the position detection system's coordinate system. In particular, position and orientation of the calibration device's localizer can be determined with a position detection system and used by a calibration unit for calculating a distance between the calibration device and at least one of the two localizers, e.g., when the medical instrument's tip is in contact with the calibration device.

The medical instrument can be a medical screwdriver with a medical screw, e.g., a bone screw, attached at the screwdriver's distal end. The medical screwdriver's lumen with the arranged sensor carrier, preferably, extends from the proximal end of the screwdriver to the distal end of the attached screw. In particular, if the medical instrument is a medical screwdriver with a medical screw, the method for automatically identifying a medical instrument can comprise the step of determining the length of the medical screw.

The step of determining the length of the medical screw, preferably, comprises the sub-steps of contacting the calibration device with a tip of the medical screw, and, when in contact, determining position and orientation of the at least two localizers, calculating a distance between the calibration device and at least one of the two localizers based on the determined position and orientation, and determining the length of the screw at least from the calculated distance and using at least the determined length for identifying the medical screw.

Additionally, or alternatively, the method for automatically identifying a medical instrument can comprise the steps of rotating the sensor carrier at least by 180°, preferably, by 360°, around its longitudinal axis, and, at the same time, determining position and orientation of the at least to localizers and using the determined positions and orientations to calculate a centering error and/or a positioning error and/or an angle error.

In particular, in variants of the method for automatically identifying a medical instrument in which a centering error and/or a positioning error and/or an angle error is calculated, preferably, the method can comprise the further step of compensating for the calculated centering error and/or positioning error and/or angle error when calculating the distance between the calibration device and at least one of the two localizers.

In particular, if the sensor carrier comprises at least a third localizer that is configured for providing a sensor signal representing position and orientation of the third localizer, the third localizer being arranged at a distance from the first and second localizers towards the sensor carrier's proximal end, the method for automatically identifying a medical instrument can comprise the further steps of determining position and orientation of the third localizer, calculating an angle of a medical instrument from the position and orientation of the third localizer and position and orientation of at least one of the first and second localizers, and using the calculated angle for identifying the medical instrument.

Preferably, the medical instrument's lumen in which the sensor carrier is arranged is an off-centric lumen. Thereby, the medical instrument can comprise further lumens that can be used for different purposes, even, when the sensor carrier is arranged in the off-centric lumen.

According to the invention a method for treating a herniated disc and, in particular, a method of removing at least a part of an intervertebral disc and/or surrounding body tissue is proposed.

The method of removing at least a part of an intervertebral disc and/or surrounding body tissue can be conducted, e.g., using the surgical kit comprising an access needle, a guidewire, a guiding rod, at least one dilation tube, a working tube, a reamer, an endoscope, and a medical instrument that is configured to be arranged inside the endoscope's working channel and for removing at least a part of an intervertebral disc and/or surrounding body tissue.

The method of removing at least a part of an intervertebral disc and/or surrounding body tissue according to the invention comprises the steps of providing a sensor carrier, configured to be removably arranged in a lumen of a medical instrument, the sensor carrier having at least two localizers, the localizers each being configured for providing a sensor signal representing position and orientation of the respective localizer, inserting the sensor carrier into a lumen of an access needle, calibrating the access needle with arranged sensor carrier, navigating the access needle with arranged sensor carrier inside a patient's body to a spine's vertebra, in particular, to a disc space of the spine, and, at the same time, determining position and orientation of the at least two localizers from sensor signals and indicating the position at least of the tip of the access needle in a patient model visualized on a monitor using the determined position and orientation of the localizers, removing the sensor carrier from the access needle's lumen and, subsequently, inserting a guidewire into the access needle's lumen, removing the access needle from the guidewire such that only the guidewire stays inside the patient's body, inserting the sensor carrier into a lumen of a guiding rod and calibrating the guiding rod, removing the sensor carrier from the guiding rod and advancing the guiding rod over the guidewire up to the vertebra, in particular, to the facet joint of the vertebra, removing the guidewire from the guiding rod and inserting the sensor carrier into the guiding rod, when getting close to the facet joint, indicated by increased resistance, navigating the guiding rod with arranged sensor carrier to the vertebra's facet joint and, at the same time, determining position and orientation of the at least two localizers and indicating the position at least of the distal tip of the guiding rod in a patient model visualized on a monitor using the determined position and orientation of the localizers, removing the sensor carrier from the guiding rod, advancing at least one dilation tube over the guiding rod, wherein the dilation tube is configured for dilating an access path to the vertebra, inserting the sensor carrier into a lumen of a working tube, wherein at its distal end the working tube is shaped such that at its distal end the working tube can be anchored to a patient's bone, calibrating the working tube, removing the sensor carrier from the working tube, advancing the working tube over the dilation tube towards the facet joint removing the guiding rod and the dilation tube, when the working tube is close to the facet joint, indicated by increased resistance, inserting the sensor carrier and anchoring the working tube with its distal end to the vertebra, and, at the same time, determining position and orientation of the at least two localizers and indicating the position at least of the distal tip of the working tube in a patient model visualized on a monitor using the determined position and orientation of the localizers, removing the sensor carrier from the working tube, inserting the sensor carrier together with an endoscope into a reamer's lumen, afterwards, inserting the reamer with sensor carrier and endoscope into the working channel of the working tube and using the reamer for creating a posterior-lateral access to the central nervous system, and, at the same time, determining position and orientation of the at least two localizers and indicating the position at least of the distal tip of the reamer in a patient model visualized on a monitor using the determined position and orientation of the localizers, and removing at least a part of an intervertebral disc and/or surrounding body tissue through an endoscope working channel of the endoscope.

Creating a posterior-lateral access to the central nervous system, preferably, comprises reaming of a small part of the facet joint of the vertebra. Alternatively to a reamer, also a drill can be used for creating a posterior-lateral access to the central nervous system.

For creating a posterior-lateral access to the central nervous system, the Kambin's triangle approach can be used.

Within the framework of the specification, "navigating medical instrument" includes guiding the medical instrument with arranged sensor carrier relative to an object and tracking the position of the medical instrument with a position detection system by means of determining position and orientation of a sensor carrier's localizers.

Preferably, while removing an intervertebral disc through a working channel of the endoscope, position and orientation of the at least two localizers are determined and used for indicating the position at least of the distal tip of the endoscope in a patient model visualized on a monitor.

The method of removing at least a part of an intervertebral disc and/or surrounding body tissue can comprise the step of—after inserting the sensor carrier into the lumen of at least one of the access needle, the guiding rod, the working tube, the reamer or the endoscope—automatically identifying the medical instrument having the sensor carrier arranged in its lumen by determining a distance between medical instrument's distal tip and the position of at least one of the two localizers, determining a length of the lumen of the respective medical instrument based on the determined distance and identifying the medical instrument with the arranged sensor carrier based on the determined length of its lumen.

Optionally, the method of removing at least a part of an intervertebral disc and/or surrounding body tissue comprises the step of displaying on a monitor a visualisation of a patient model with the position of at least one of the access needle, the guiding rod, the working tube, the working tube, the reamer, or the endoscope indicated in the model, and/or an endoscope image captured by the endoscope based on whether or not the sensor carrier and/or the endoscope is used in a particular method step and/or based on whether or not a relative movement between sensor carrier and vertebra is detected.

According to the invention, also a method for spinal fusion and, in particular, a method of fusing at least two vertebrae is proposed.

The method of fusing at least two vertebrae can be conducted with, e.g., the surgical kit according to the invention comprising an access needle, a lamina screwdriver with lamina screw, a tap, and a pedicle screwdriver, and a spine cage.

The method of fusing at least two vertebrae according to the invention comprises the steps of providing a sensor carrier, configured to be removably arranged in a lumen of a medical instrument, the sensor carrier having at least two localizers, the localizers each being configured for providing a sensor signal representing position and orientation of the respective localizer, providing a working tube with a working channel, the working tube being arranged inside a patient's body to provide a posterior-lateral access to a disc space between two vertebrae, wherein at least a part of an intervertebral disc and/or surrounding body tissue has been removed from the disc space, —using the working tube's working channel for implanting a spine cage into a patient's spine for restoring the disc space between the two respective vertebrae, inserting the sensor carrier into an access needle and navigating the access needle with arranged sensor carrier to one of the vertebra's Lamina, and, at the same time, determining position and orientation of the at least two localizers and indicating the position at least of the distal tip of the access needle in a patient model visualized on a monitor using the determined position and orientation of the localizers, drilling of a vertebras lamina with the access needle, and, at the same time, determining position and orientation of the at least two localizers, and, at the same time, determining position and orientation of the at least two localizers and indicating the position at least of the distal tip of the access needle in a patient model visualized on a monitor using the determined position and orientation of the localizers, removing the sensor carrier from the access needle and, subsequently, inserting the sensor carrier into a lumen of a lamina screwdriver having a lamina screw attached such that at least one of the sensor carrier's localizers is located at least close to lamina screw's distal tip, implanting the lamina screw in the vertebra's Lamina with the sensor carrier being arranged in Lamina screwdriver and lamina screw, and, at the same time, determining position and orientation of the at least two localizers and indicating the position at least of the distal tip of the lamina screw in a patient model visualized on a monitor using the determined position and orientation of the localizers, removing the sensor carrier from the screwdriver, afterwards, inserting the sensor carrier into a lumen of an access needle and navigating the access needle with arranged sensor carrier to one of the Pedicles of the vertebra, and, at the same time, determining position and orientation of the at least two localizers and indicating the position at least of the distal tip of the access needle in a patient model visualized on a monitor using the determined position and orientation of the localizers, removing the sensor carrier from the access needle, afterwards, inserting the sensor carrier into a lumen of a tap and tapping a tapped hole into the vertebra's Pedicle, and, at least while tapping, determining position and orientation of the at least two localizers and indicating the position at least of the distal tip of the tap in a patient model visualized on a monitor using the determined position and orientation of the localizers, removing the sensor carrier from the tap, subsequently, inserting the sensor carrier into a lumen of a pedicle screwdriver with pedicle screw and placing the pedicle screw into the vertebra's Pedicle, and, at least while placing the screw, determining position and orientation of the at least two localizers and indicating the position at least of the distal tip of the pedicle screw in a patient model visualized on a monitor using the determined position and orientation of the localizers, and using the sensor carrier, an access needle, a tap and a pedicle screwdriver with another pedicel screw for placing the other pedicle screw in one of the neighbouring vertebrae and connecting the at least two pedicle screws placed in the vertebrae with a rod in order to fuse the two neighbouring vertebrae.

The step of providing a working tube with a working channel, the working tube being arranged inside a patient's body to provide a posterior-lateral access to a disc space between two vertebrae, wherein at least a part of an intervertebral disc and/or surrounding body tissue has been removed from the disc space can comprise conducting the steps of the method of removing at least a part of an intervertebral disc and/or surrounding body tissue according to the invention as described above.

Preferably, for implanting the cage, the position of the cage is tracked relative to the position and orientation of the at least two localizers of the sensor carrier and indicated in a patient model visualized on a monitor.

The method of fusing at least two vertebrae can further comprise the step of automatically detecting at least the lamina screw length and/or the pedicle screw length of the lamina screw and pedicle screw, respectively, by arranging the sensor carrier in the lumen of the screwdriver with attached bone screw such that the at least two localizers are arranged at a distance to each other along the longitudinal axis of the screwdriver, determining a distance between the screw's distal tip and the positions of at least one of the two localizers based on position and orientation of the at least two localizers, and automatically detecting the length of the screw based on the determined distance.

Automatically detecting at least the lamina screw length and/or the pedicle screw length of the lamina screw and pedicle screw, respectively, can be perform with a calibration unit of the medical instrument identification setup as described above.

In particular, if at least the lamina screw length and/or the pedicle screw length of the lamina screw and pedicle screw are automatically detected, the method of fusing at least two vertebrae can comprise the further step of assigning the determined screw length to one out of a plurality of predefined screw types for identifying the screw. Assigning the determined screw length to one out of a plurality of predefined screw types for identifying the screw can be conducted, e.g., with a medical instrument identification unit of the medical instrument identification setup as described above. For example, it is possible to distinguish between different screw types by using various different pre-calibrated sensor carriers, e.g., sensor carriers with different lengths, different arrangements of localizers, or different number of localizers. Preferably, a sensor carrier of the various different pre-calibrated sensor carriers can be configured such that with this sensor carrier it is only possible to calibrate screws of a specific pre-set of screws of a plurality of different pre-sets of screws. Another sensor carrier of the various different pre-calibrated sensor carriers can be configured such that with this sensor carrier it is only possible to calibrate screws of another pre-set of screws of the plurality of different pre-sets of screws. Thereby, it is possible for identifying a pre-set of screw by determining that sensor carrier of various different pre-calibrated sensor carriers with which the pre-set of screw can be calibrated.

Accordingly, a medical instrument identification setup's medical instrument identification unit can be configured for identifying a medical screw by determining that sensor carrier of various different pre-calibrated sensor carriers with which the medical screw of a pre-set of screw can be calibrated on a calibration device by means of a calibration unit.

In some variants of the method of fusing at least two vertebrae, the at least two localizers of the sensor carrier are arranged close to the distal tip of the sensor carrier and the sensor carrier comprises at least a third localizer that is arranged at a distance to the at least two localizers towards the sensor carrier's proximal end. If the sensor carrier comprises at least a third localizer, the method of fusing at least two vertebrae, preferably, comprises the further step of determining a bending of the access needle with the sensor carrier arranged in its lumen by calculating a bending angle enclosed between at least one of the at least two localizers and the at least third localizer based on determined positions and orientations the localizers.

In particular, if within the method of fusing at least two vertebrae a bending angle enclosed between at least one of the at least two localizers and the at least third localizer is calculated, the method can comprise the step of visualizing a digital representation at least of a part of the access needle on a monitor in a bended state according to the calculated angle.

BRIEF DESCRIPTION OF THE DRAWINGS

In the following, preferred embodiments of the invention are described with reference to the figures. In the figures.

DETAILED DESCRIPTION

Figure 1:
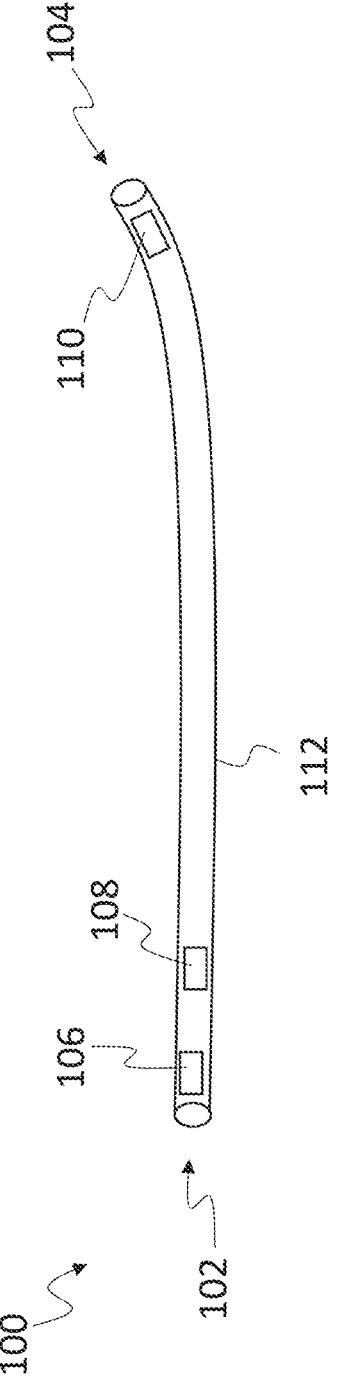
FIG. 1: schematically shows a sensor carrier for connecting a medical instrument to a position detection system.

FIG. 1 schematically shows a sensor carrier 100 for connecting a medical instrument to a position detection system. For connecting a medical instrument to a position detection system, the sensor carrier 100 can be inserted into a medical instrument's lumen. With the sensor carrier 100 being arranged in a medical instrument's lumen, a navigated procedure can be performed and the position of the medical instrument, e.g., inside a patient's body, can be tracked and displayed on a monitor. After having accomplished a navigated procedure, the sensor carrier can be removed from the medical instrument's lumen and inserted into the lumen of another medical instrument for connecting the other medical instrument to the position detection system.

The sensor carrier 100 has a distal end 102 and a proximal end 104. The sensor carrier 100 comprises three localizers 106, 108, 110 that are arranged along the length of the sensor carrier 100. The localizers 106, 108, 110 each are configured for providing a sensor signal representing position and orientation of the respective localizer 106, 108, 110. For example, each of the localizers 106, 108, 110 can comprise at least one sensor coil, for connecting a medical instrument with arranged sensor carrier 100 to an electromagnetic position detection system.

Close to the sensor carrier's proximal end 102, a first localizer 106 of the three localizers is arranged. A second localizer 108 of the three localizers is arranged at a distance from the first localizer 106 towards the proximal end 104 of the sensor carrier 100. The sensor carrier 100 further comprises a third localizer 110 that is arranged at a distance from the first and second localizers 106, 108 towards the sensor carrier's proximal end 104. The third localizer 110 of the three localizers is optional and is not present in alternative embodiments of the sensor carrier 100.

The sensor carrier 100 having three localizers 106, 108, 110 is particularly suitable for identifying a medical instrument having an angle that is characteristic for the medical instrument. Preferably, for calculating an angle of a medical instrument, the sensor carrier 100 is arranged in the medical instrument's lumen such that the medial instrument's angle is located between the third localizer 110 and the first and second localizers 106, 108. From position and orientation determined for the localizers 106, 108, 110, respectively, the angle of the medical instrument can be calculated, e.g., with a calibration unit of a medical instrument identification setup, and used by a medical instrument identification setup's medical instrument identification unit for identifying the medical instrument with the sensor carrier 100 arranged in its lumen.

The sensor carrier 100 further comprises a hypo tube 112 extending from the distal end 102 to the proximal end 104 of the sensor carrier 100 and enclosing the three localizers 106, 108, 110. The hypo tube 112 is configured to give mechanical stability to the sensor carrier 100 and to protect the localizers 106, 108, 110 from external influences.

Figure 2:
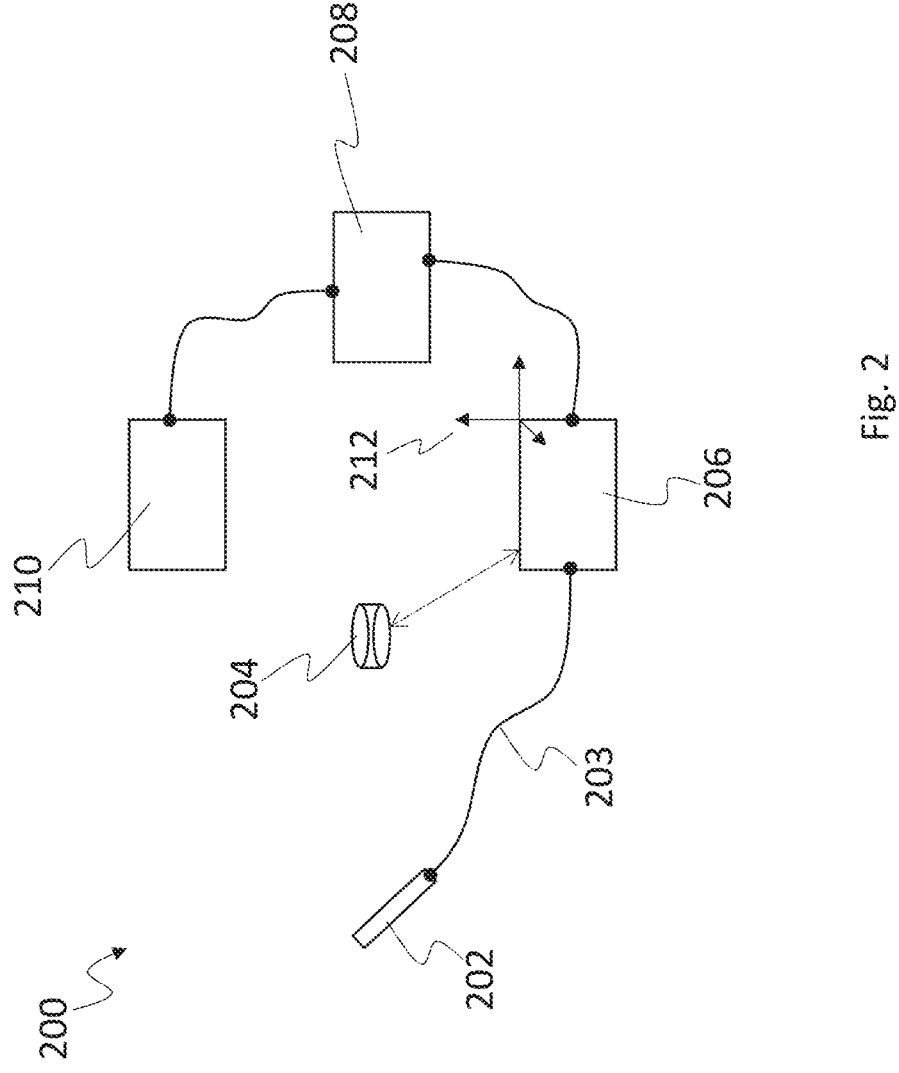
FIG. 2: schematically shows a medical instrument identification setup, comprising a sensor carrier and a calibration device.

FIG. 2 schematically shows a medical instrument identification setup 200 comprising a sensor carrier 202, a calibration device 204, a position detection system 206, a calibration unit 208, and a medical instrument identification unit 210.

The sensor carrier 202 can be configured the same way as the sensor carrier described with reference to FIG. 1. In particular, the sensor carrier 202 has at least two localizers (not shown) and can optionally have at least a third localizer that, preferably, is arranged close to the sensor carrier's proximal end. The localizers each are configured for providing a sensor signal representing position and orientation of the respective localizer. The sensor carrier 202 is configured to be removably arranged in a lumen of a medical instrument for connecting the medical instrument to the position detection system 206.

The sensor carrier 202 is connected to the position detection system 206 via a cable 203. In some embodiments of the medical instrument identification setup 200 provision is made of a sensor carrier that can be wirelessly connected to the position detection system 206. Via the cable 203, sensor signals provided by the localizers of the sensor carrier 202 can be transmitted to the position detection system 206. The position detection system 206 is configured for determining position and orientation of the localizers of the sensor carrier 202 in the position detection system's coordinate system 212 from received sensor signals.

For example, the position detection system 206 can be an electrometric position detection system having a field generator for generating an alternating electromagnetic field. For determining position and orientation of the sensor carrier's localizers, the localizers, preferably, comprise one or more sensor coils. When exposed to an alternating electromagnetic field, a voltage is induced in each of the coils that depends on position and orientation of the respective sensor coils in the alternating electromagnetic field. A sensor signal representing the induced voltage can be tapped from each of the sensor coils and transmitted to the position detection system for determining position and orientation of the sensor coils, respectively.

The calibration device 204 of the medical instrument identification setup 200 is configured such that its position and orientation in the position detection system's coordinate system 212 can be determined by the position detection system 206. For example, the calibration device 204 can be arranged at a position whose coordinate is known in the position detection system's coordinate system 212. It is also possible that the calibration device 204 is equipped with one or more localizers, the position and orientation of which can be directly determined with the position detection system 206. The calibration device 204, preferably, is connected to the position detection system 206 for transmitting sensor signals representing position and orientation of the calibration device to the position detection system.

The position detection system 206 is connected to the calibration unit 208 for providing determined positions and orientations of localizers. The calibration unit 208 is configured for calibrating a medical instrument with the sensor carrier 202 arranged in its lumen by calculating a distance between the medical instrument's tip and at least one of the sensor carrier's localizers. The calibration unit 208 is configured for using the position and orientation of the calibration device 204 known in the position detection system's coordinate system 212 and position and orientation of at least one of the sensor carrier's localizers as determined by the position detection system 206. Preferably, the calibration unit is configured for determining whether or not the medical instrument's tip is in contact with the calibration device 204. Preferably, the calibration unit is configured for using position and/or orientation of at least one of the sensor carrier's localizers which have been determined with the position detection system 206 at a moment of contact between the medical instrument's tip and the calibration device 204.

Since the distance between the medical instrument's tip and at least one of the sensor carrier's localizers is characteristic for the length of the lumen of a medical instrument, from a calculated distance the length of a lumen can be derived. Furthermore, since the length of a medical instrument's lumen is characteristic for the medical instrument itself, the determined length of a medical instrument's lumen can be used for automatically identifying the medical instrument having the sensor carrier 202 arranged in its lumen.

For identifying a medical instrument having the sensor carrier 202 arranged in its lumen, the medical instrument identification setup 200 comprises the medical instrument identification unit 210 that is connected to the calibration unit 208 for obtaining a calculated distance between a medical instrument's tip and at least one of the sensor carrier's localizers. The medical instrument identification unit 210 is configured for determining a length of the medical instrument's lumen at least from a distance between a medical instrument's tip and at least one of the sensor carrier's localizers as calculated by the calibration unit 208. The medical instrument identification unit 210 is configured for using the determined length of the medical instrument's lumen for identifying the medical instrument. The medical instrument identification unit 210 can be configured to alternatively or additionally to the lumen's length use a medical instrument's angle that has been calculated by the calibration unit 208 from position and orientation of at least two localizers between which the medical instrument's angle is located when the sensor carrier is arranged in the medical instrument's lumen. For identifying the medical instrument, the medical instrument identification unit 210 can be configured to compare the distance calculated by the calibration unit 208 and also the medical instrument's angle to various lengths and/or angles of a plurality of medical instruments contained in a database that can be accessed by or that is part of the medical instrument identification unit 210.

Figure 3:
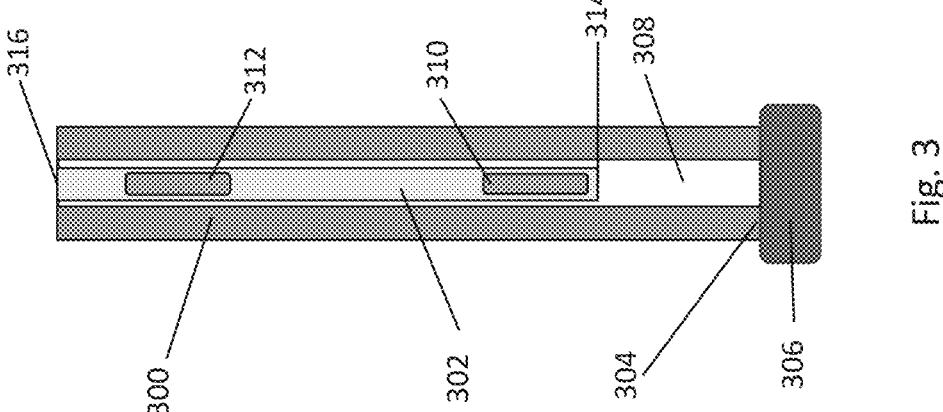
FIG. 3: schematically shows a medical instrument with sensor carrier, the medical instrument contacting a calibration device.

FIG. 3 schematically shows a medical instrument 300 with sensor carrier 302. The medical instrument's tip 304 is in contact with a calibration device 306. The medical instrument 300 has a lumen 308 extending from the medical instrument's proximal end to its distal end. In the lumen 308 the sensor carrier 302 is arranged. The sensor carrier 302 comprises two localizers 310, 312, a first localizer 310 of the two localizers being arranged at the distal end 314 of the sensor carrier 302 and a second localizer 312 being arranged at a distance from the first localizer 310 towards the sensor carrier's proximal end 316.

Having two localizers arranged in the distal end region of the sensor carrier is of advantage since it facilitates determining the trueness of the medical instrument's virtual longitudinal axis to the physical instrument's longitudinal axis. The virtual longitudinal axis can be extrapolated from the distal end of the sensor carrier to the distal end of the medical instrument to thus determine the position of the medical instrument's distal end. The medical instrument's virtual longitudinal axis can also be displayed in sectional images on a monitor. Displaying the virtual longitudinal axis in sectional images on a monitor is of importance, e.g., when aiming with a medical instrument at an anatomical target from a large distance, e.g., from 5 to 15 cm. With an accurately displayed virtual longitudinal axis, e.g., of an access needle, a surgeon can assess position and orientation of the needle to reliably navigate the needle to a target location.

The virtual longitudinal axis can also be determined by the position detection system and/or the calibration unit in case one localizer implements a 5 DOF sensor. However, using one 5 DOF sensor to determine the medical instrument's virtual longitudinal axis typically is subject to an angle error of the coil, an error introduced by the physical alignment inside the sensor carrier and an error introduced by the physical alignment of the sensor carrier inside the instrument. This can lead to angle errors between 4° and 5°.

Advantageously, when using two localizers each implementing a 5 DOF sensor, e.g., by using sensor coils, it is possible to reduce the angle error to only the position error of both sensor coils. Spacing the sensor coils 100 mm apart from each other, and having position errors of less than 1 mm, it is possible to reduce the angle error to less than 1° $(\tan(\frac{1}{100}))$.

The length of the sensor carrier 302 is shorter than the length of the medical instrument 300 such that there exists a non-zero distance between the sensor carrier's distal end 314 and the medical instrument's tip 304. The distance is characteristic for the medical instrument and can be used for determining the length of the medical instrument's lumen 308. Since the length of the medical instrument's lumen 308 is characteristic for the medical instrument 300 itself, by means of the length of the medical instrument's lumen 308 the medical instrument 300 with arranged sensor carrier 302 can be identified.

The medical instrument 300 can be a medical instrument that has a lumen 308 provided, e.g., for advancing the medical instrument 300 over a guidewire. For example, the medical instrument 300 can be an access needle, a guiding rod, a working tube, tap, a balloon dilation device, or a screwdriver.

The sensor carrier 302 can be configured the same way as the sensor carrier described with reference to FIG. 1 or as the sensor carrier described with reference to FIG. 2. In particular, the sensor carrier 302 and the calibration device 306 can be elements of a medical instrument identification setup, e.g., of a medical instrument identification setup as described with reference to FIG. 2.

Figure 4:
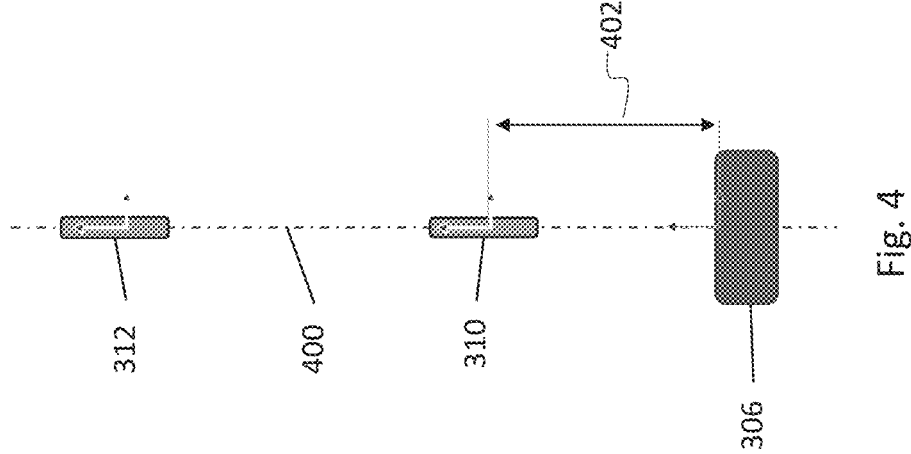
FIG. 4: refers to the geometrical arrangement of the sensor carrier's localizers, medical instrument and the calibration device as schematically depicted in FIG. 3, FIG. 5: schematically shows a screwdriver with an attached pedicle screw and a sensor carrier being arranged in the screwdriver's and the pedicle screw's lumen, the pedicle screw being in contact with a calibration device.

FIG. 4 refers to the geometrical arrangement of the sensor carrier's localizers 310, 316, medical instrument and the calibration device 306 as described with reference to FIG. 3.

The two localizers 310, 316 are arranged at a distance to each other along the longitudinal axis 400 of the medical instrument 300.

For automatically identifying the medical instrument 300, the distance 402 between the calibration device 306 and the localizer 310 that is arranged close to the sensor carrier's distal end is calculated, e.g., by means of a calibration unit as described with reference to FIG. 2. For calculating the distance 402, preferably, position and orientation of the calibration device 306 and position and orientation of the localizer 310 as determined by a position detection system, e.g., of a medical instrument identification setup, can be used.

In particular, position and orientation of the localizer 310 can be determined when the medical instrument's tip is in contact with the calibration device 306 and used for calculating the distance 402. Advantageously, if the medical instrument's tip is in contact with the calibration device 306, the position of the medical instrument's tip can directly be determined from position and orientation of the calibration device 306.

Position and orientation of the second localizer 312 can be used as a reference for performing a plausibility check on the calculated distance 402. Position and orientation of the first localizer 310 and the second localizer 312 can also be used for calculating a centering error and/or a positioning error and/or an angle error. The calculated centering error and/or positioning error and/or angle error can be compensated by the calibration unit when calculating the distance 402 between the calibration device and the localizer 310. Thereby it is possible to calculate the distance 402 between the calibration device 306 and the localizer 310 with improved accuracy with the calibration unit.

Having calculated the distance 402 between the calibration device 306 and the localizer 310, the distance 402 can be used for determining the length of the medical instrument's lumen 308 based on which the medical instrument 300 itself can be identified.

Figure 5:
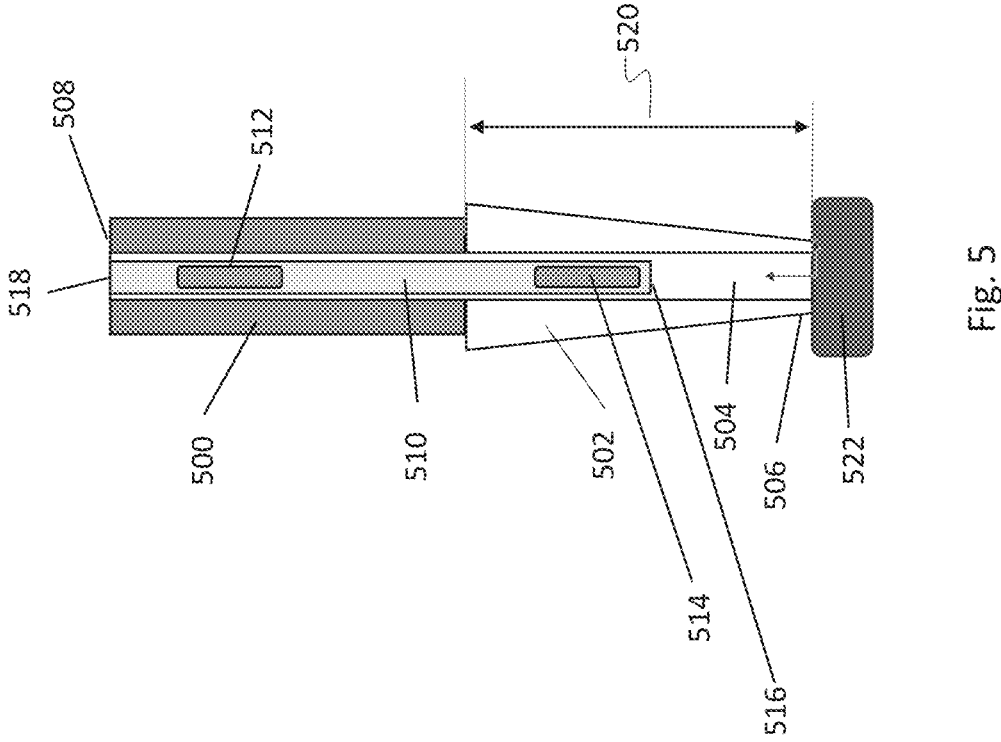

As shown in FIG. 3, in FIG. 5, a medical instrument with arranged sensor carrier is shown schematically, the medical instrument contacting a calibration device.

In FIG. 5, the medial instrument is a screwdriver 500 with an attached medical screw 502, e.g., a bone screw, preferably, a pedicle screw.

A lumen 504 extends from the screwdriver's proximal end 506 to the medical screw's distal end 508. In the lumen 508, the sensor carrier 510 is arranged. The sensor carrier 510 comprises two localizers 512, 514 wherein a first localizer 512 is arranged close to the sensor carrier's distal end 516 and the second localizer is arranged at a distance from the first localizer 516 towards the sensor carrier's proximal end 518. The sensor carrier 510 can be configured the same way as the sensor carrier as described with reference to FIG. 1 or with reference to FIG. 2.

The medical screw 502 has a length 520 that is characteristic for the medical screw 502. Thus, by determining the length of the screw, on the basis of the screw length the medical screw 502 itself can be identified.

With its distal end 506, the medical screw 502 is in contact with the calibration device 522 for calibrating the screwdriver 500, e.g., with a calibration unit of a medical instrument identification setup, e.g., as described with reference to FIG. 2. Calibrating the screwdriver comprises determining a distance 600 between the calibration device 522 and the first localizer 512 as depicted in FIG. 6.

Figure 6:
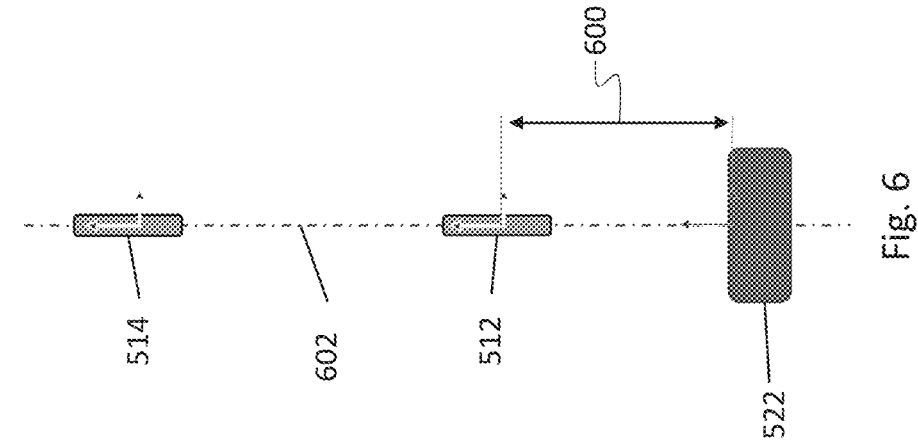
FIG. 6: refers to the geometrical arrangement of the sensor carrier's localizers, the screwdriver and the calibration device as schematically depicted in FIG. 5, FIG. 7: shows a flow diagram representing a method for automatically identifying a medical instrument.

FIG. 6 refers to the geometrical arrangement of the sensor carrier's localizers 512, 514, the screwdriver and the calibration device 522 as schematically depicted in FIG. 5. The localizers 512, 514 are arranged along the screwdriver's longitudinal axis 602. In particular, position and orientation of the first localizer 512 are used for calculating the distance 600 to the calibration device which corresponds to the distance between the first localizer 512 and the medical screw's distal end 506.

The distance 600 is characteristic for the length of the medical screw 502. Therefore, the determined distance 600 can be used for automatically identifying the medical screw 502. For example, for identifying the medical screw 502 based on the determined distance 600, the length of the screwdriver 500 and the length of the sensor carrier 510 can be used. It can also be exploited that the positions of the localizers relative to each other are fixed. Preferably, the first localizer 512 is arranged close to the sensor carrier's distal end such that by determining the first localizer's position and orientation, position and orientation of the sensor carrier's distal end can be obtained.

The calibration device 522 and the sensor carrier 510 can be elements of a medical instrument identification setup, in particular, of a medical instrument identification setup as described with reference to FIG. 2.

Figure 7:
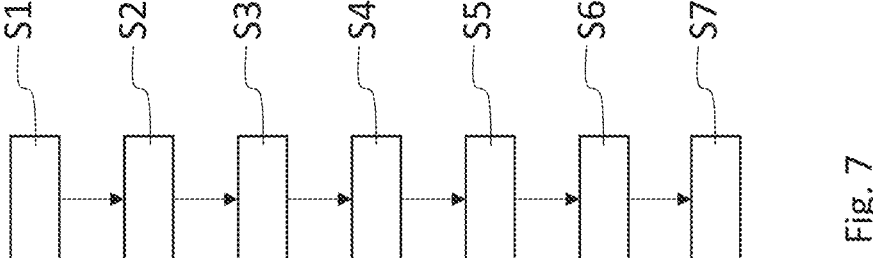

FIG. 7 shows a flow diagram representing a method for automatically identifying a medical instrument.

Initially, a sensor carrier is provided (step S1) which is configured to be removably arranged in a lumen of a medical instrument. The sensor carrier has at least two localizers. The localizers each are configured for providing a sensor signal representing position and orientation of the respective localizer. The sensor carrier can be a sensor carrier as described with reference to FIG. 1, or with reference to FIG. 2, or a sensor carrier as described with reference to FIG. 3 or 5.

A calibration device is provided (step S2), the position and orientation of which is known in the coordinate system of a position detection system. For example, the calibration device can be arranged at a position whose coordinate is known in the position detection system's coordinate system. It is also possible that the calibration device comprises one or more localizers that are configured for providing a sensor signal representing position and orientation of the calibration device.

The sensor carrier is inserted into a lumen of a medical instrument (step S3). The medical instrument having a lumen can, e.g. be a catheter, a Jamshidi needle, a tap, a screwdriver with an attached bone screw, e.g., a pedicle screw, that can be placed with the screwdriver into a patient's bone, or another cannulated medical instrument. After insertion, the sensor carrier is removably arranged in the medical instrument's lumen and can, thus, be removed after having accomplished a task with the medical instrument and used for connecting another medical instrument to a position detection system.

Position and orientation of the at least two localizers are determined from provided sensor signals (step S4). For example, the localizers can comprise one or more sensor coils the position of which can be determined with an electromagnetic position detection system having a field generator for generating an alternating electromagnetic field. When exposed to a generated electromagnetic field, a voltage is induced representing position and orientation of the sensor coils. From a tapped sensor signal representing the induced voltage, position and orientation of the sensor coils can be determined by the position detection system in the position detection system's coordinate system.

A distance between the calibration device and at least one of the two localizers is calculated (step S5) based on the determined position and orientation of the localizers to calibrate the medical instrument. Preferably, the distance is calculated based on position and orientation of the localizers determined when the medical instrument's tip is contacting a calibration device.

Afterwards, in step S6, the length of the medical instrument's lumen is determined at least from the calculated distance. In particular, the distance between the calibration device and at least one of the two localizers is characteristic for the length of the medical instrument's lumen and, thus, for the medical instrument itself.

Subsequently, in step S7, at least the determined length of the lumen is used for automatically identifying the medical instrument with the sensor carrier being arranged in its lumen. Additionally, also a medical instrument's angle and/or a length of that section of the sensor carrier that extends beyond the medical instrument's proximal end can be used for identifying the medical instrument. For identifying the medical instrument, the determined length of the lumen can be compared with entries of a database representing lengths of lumens of different medical instruments, e.g., of medical instruments of a surgical kit that is used during surgery.

If a medical instrument is automatically identified, e.g., by a medical instrument identification setup, settings, e.g., the mode of displaying the medical instrument on a monitor can be adapted accordingly.

The method can be conducted with a medical instrument identification setup, in particular, with a medical instrument identification setup as described with reference to FIG. 2.

Figure 8:
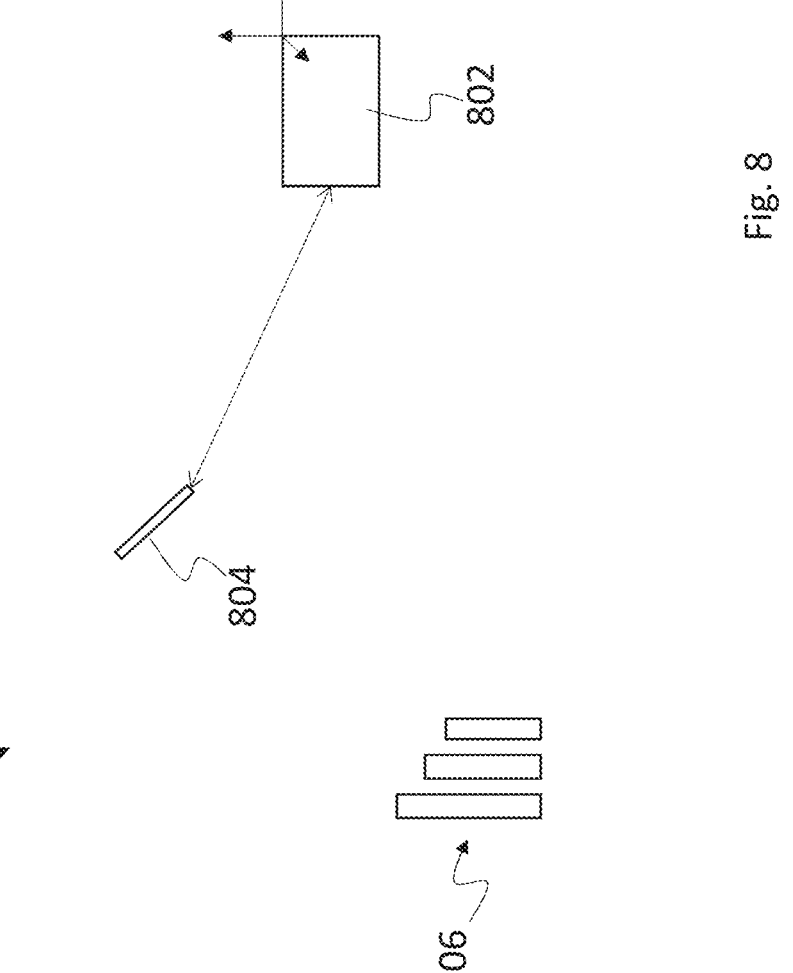
FIG. 8: shows schematically a surgical kit for performing minimally invasive spine surgery.

FIG. 8 schematically shows a surgical kit 800 for performing minimally invasive spine surgery.

The surgical kit 800 comprises a position detection system 802, a sensor carrier 804 that is operatively connected to the position detection system 802, and a plurality of medical instruments each having a lumen 806 in which the sensor carrier 804 can be arranged for connecting the respective medical instrument to the position detection system 802.

The sensor carrier 804 is configured to be removably arranged in a lumen of one medical instrument of the plurality of medical instruments 806. The sensor carrier 804 has at least two localizers, the localizers each being configured for providing a sensor signal representing position and orientation of the respective localizer. The sensor carrier 802 can be configured the same way as the sensor carrier described with reference to FIG. 1 or the sensor carrier described with reference to FIG. 3 or 5. In particular, the sensor carrier can have at least a third localizer that is arranged at or at least close to the sensor carrier's proximal end.

The position detection system 802 is configured for detecting position and orientation of localizers from respectively provided sensor signals in the position detection system's coordinate system. Preferably, an electromagnetic position detection system is used and the sensor carrier's localizers are equipped with sensor coils.

Advantageously, the surgical kit 800 can comprise or can be used in combination with a medical instrument identification setup, preferably, with the medical instrument identification setup as described with reference to FIG. 2. When using the surgical kit 800 in combination with medical instrument identification setup as described with reference to FIG. 2, the surgical kit's position detection system 802 and the sensor carrier 804 can also be the position detection system and the sensor carrier of the medical instrument identification setup, respectively.

A medical instrument of the plurality of medical instruments 806 having a lumen in which the sensor carrier 804 can be removably arranged for connecting the respective medical instrument to the position detection system 802 can, e.g., be an access needle, a guiding rod, a working tube, a reamer, an endoscope, a lamina screwdriver with lamina screw, a tap, or a pedicle screwdriver.

Figure 9:
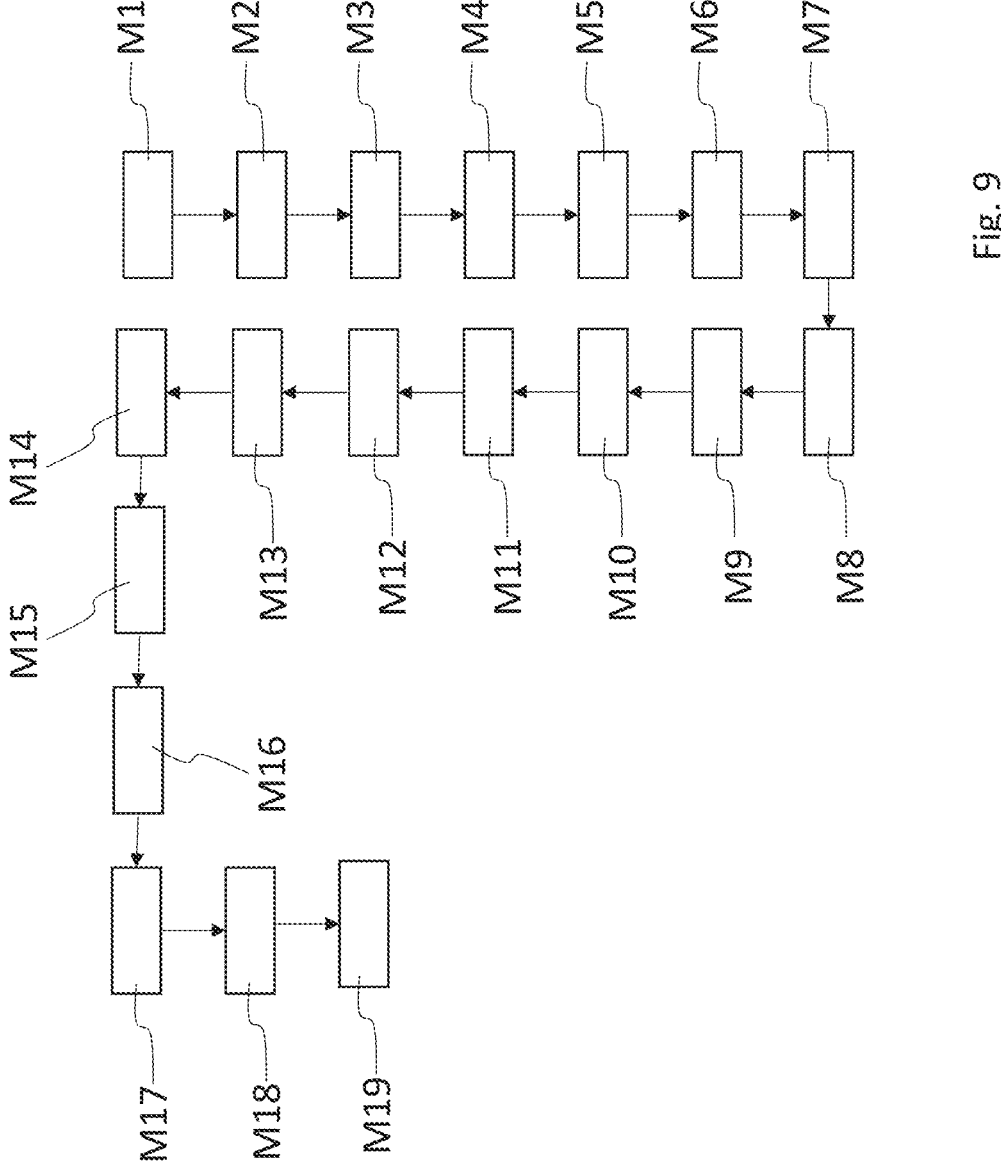
FIG. 9: shows a flow diagram representing a method of removing at least a part of an intervertebral disc and/or surrounding body tissue.

If the surgical kit 800 comprises an access needle, a guidewire, a guiding rod, at least one dilation tube, a working tube, a reamer, an endoscope, and a medical instrument that is configured to be arranged inside the endoscope's working channel and for removing at least a part of an intervertebral disc and/or surrounding body tissue, the surgical kit 800 is particularly suitable for conducting the method of removing at least a part of an intervertebral disc and/or surrounding body tissue as described with reference to FIG. 9.

A medical instrument of the plurality of medical instruments 806 having a lumen in which the sensor carrier 804 can be removably arranged for connecting the respective medical instrument to the position detection system can also be an access needle, a lamina screwdriver with lamina screw, a tap, and a pedicle screwdriver, is particularly suitable. If the surgical kit 800 comprises an access needle, a lamina screwdriver with lamina screw, a tap, and a pedicle screwdriver, and a spine cage, the surgical is particularly suitable for conducting the of fusing at least two vertebrae as described with reference to FIG. 10.

FIG. 9 shows a flow diagram representing a method of removing at least a part of an intervertebral disc and/or surrounding body tissue.

Initially, a sensor carrier is provided (step M1) that is configured to be removably arranged in a lumen of a medical instrument, the sensor carrier having at least two localizers, the localizers each being configured for providing a sensor signal representing position and orientation of the respective localizer.

The sensor carrier is inserted into a lumen of an access needle (step M2).

Subsequently, the access needle with arranged sensor carrier is calibrated on a calibration device (step M3), Afterwards, the access needle with arranged sensor carrier is navigated inside a patient's body to a spine's vertebra, and, at the same time, position and orientation of the at least two localizers from sensor signals are determined (step M4). Additionally also the position at least of the tip of the access needle is indicated in a patient model visualized on a monitor using the determined position and orientation of the localizers.

Having reached a spine's vertebra, the sensor carrier is removed from the access needle's lumen and, subsequently, a guidewire is inserted into the access needle's lumen (step M5).

In a subsequent step (step M6), the access needle is removed from the guidewire such that only the guidewire stays inside the patient's body.

The sensor carrier is then inserted into a lumen of a guiding rod and the guiding rod is calibrated on the calibration device (step M7).

Afterwards, the sensor carrier is removed from the guiding rod and the guiding rod is advanced over the guidewire up to the facet joint of the vertebra (step M8).

Having reached the facet joint of the vertebra, the guidewire is removed from the guiding rod and the sensor carrier is inserted into the guiding rod, preferably, when getting close to the facet joint, indicated by increased resistance (step M9). At the same time, position and orientation of the at least two localizers are determined. The position at least of the distal tip of the guiding rod is indicated in a patient model visualized on a monitor using the determined position and orientation of the localizers.

Subsequently, the sensor carrier is removed from the guiding rod (step M10).

After removing the sensor carrier from the guiding rod, at least one dilation tube is advanced over the guiding rod, wherein the dilation tube is configured for dilating an access path to the vertebra (step M11).

Afterwards, the sensor carrier is inserted into a lumen of a working tube (step M12), wherein at its distal end the working tube is shaped such that at its distal end the working tube can be anchored to a patient's bone.

With the sensor carrier arranged in the working tube's lumen, the working tube is calibrated on the calibration device, and afterwards the sensor carrier is removed from the working tube (step M13).

The working tube with arranged sensor carrier is then advanced over the dilation tube up to the vertebra (step M14).

Subsequently, the guiding rod and the dilation tube are removed, preferably, when the working tube is close to the facet joint, indicated by increased resistance (step M15).

The sensor carrier is then inserted into the working tube and the working tube is anchored with its distal end to the vertebra (step M16). At the same time, position and orientation of the at least two localizers are determined and the position at least of the distal tip of the working tube is indicated in a patient model visualized on a monitor using the determined position and orientation of the localizers.

Having anchored the working tube to the vertebra, the sensor carrier is removed from the working tube's lumen to provide a working channel for insertion of a medical instrument (step M17).

Subsequently, the sensor carrier is inserted together with an endoscope into a reamer's lumen. Afterwards, the reamer with sensor carrier and endoscope is inserted into the working channel of the working tube. The reamer is used for creating a posterior-lateral access to the central nervous system (step M18). At the same time, position and orientation of the at least two localizers are determined and the position at least of the distal tip of the reamer is indicated in a patient model visualized on a monitor using the determined position and orientation of the localizers.

Having created the posterior-lateral access to the central nervous system, at least a part of an intervertebral disc and/or surrounding body tissue is removed through an endoscope working channel of the endoscope (step M19).

Figure 10:
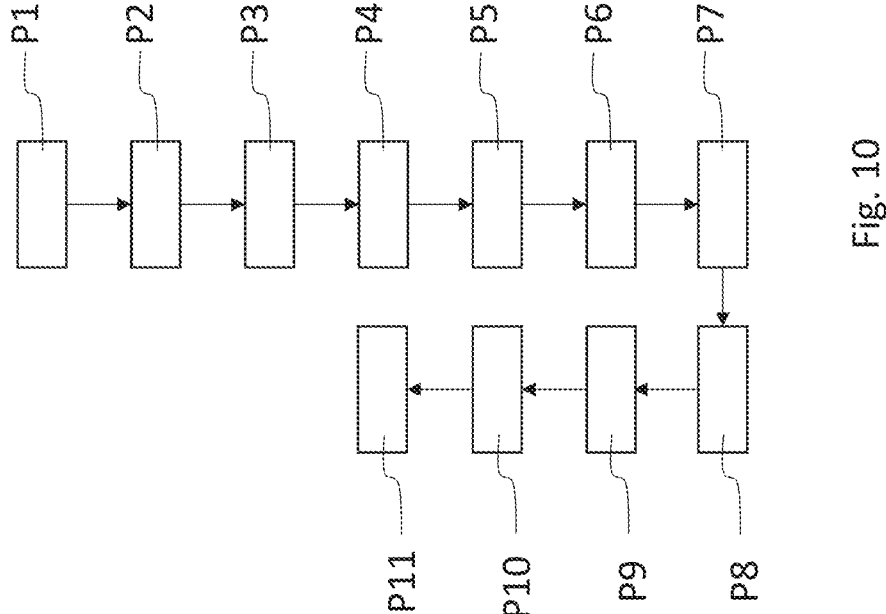
FIG. 10: shows a flow diagram representing a method of fusing at least two vertebrae.

FIG. 10 shows a flow diagram representing a method of fusing at least two vertebrae.

Initially, a sensor carrier is provided (step P1) that is configured to be removably arranged in a lumen of a medical instrument. The sensor carrier has at least two localizers, the localizers each being configured for providing a sensor signal representing position and orientation of the respective localizer.

Also, a working tube with a working channel is provided (step P2), the working tube being arranged inside a patient's body to provide a posterior-lateral access to a disc space between two vertebrae, wherein at least a part of an intervertebral disc and/or surrounding body tissue has been removed from the disc space.

The working tube's working channel is used for implanting a spine cage into a patient's spine for restoring the disc space between the two respective vertebrae (step P3).

Afterwards, the sensor carrier is inserted into an access needle and the access needle with arranged sensor carrier is navigated to one of the vertebra's Lamina (step P4). At the same time, position and orientation of the at least two localizers are determined and the position at least of the distal tip of the access needle is indicated in a patient model visualized on a monitor using the determined position and orientation of the localizers.

A successive step (step P5) comprises drilling of a vertebras facet joint with the access needle, and, at the same time, determining position and orientation of the at least two localizers and indicating the position at least of the distal tip of the access needle in a patient model visualized on a monitor using the determined position and orientation of the localizers.

Afterwards, the sensor carrier is removed from the access needle and, subsequently, the sensor carrier is inserted into a lumen of a lamina screwdriver having a lamina screw attached such that at least one of the sensor carrier's localizers is located at least close to lamina screw's distal tip (step P6).

Then, the lamina screw is implanted in the vertebra's lamina with the sensor carrier being arranged in lamina screwdriver and lamina screw (step P7), and, at the same time, position and orientation of the at least two localizers are determined and the position at least of the distal tip of the lamina screw is indicated in a patient model visualized on a monitor using the determined position and orientation of the localizers.

Afterwards, the sensor carrier is removed from the screwdriver and after that, the sensor carrier is inserted into a lumen of an access needle and the access needle with arranged sensor carrier is navigated to one of the pedicles of the vertebra (step P8). At the same time, position and orientation of the at least two localizers are determined and the position at least of the distal tip of the access needle is indicated in a patient model visualized on a monitor using the determined position and orientation of the localizers.

The sensor carrier from is then removed the access needle and, afterwards, the sensor carrier is inserted into a lumen of a tap and a tapped hole is tapped into the vertebra's pedicle, and, at least while tapping, position and orientation of the at least two localizers are determined and the position at least of the distal tip of the tap is indicated in a patient model visualized on a monitor using the determined position and orientation of the localizers (step P9).

The sensor carrier is then removed from the tap and, subsequently, the sensor carrier is inserted into a lumen of a pedicle screwdriver with pedicle screw. The Pedicle screw is placed into the vertebra's pedicle, and, at least while placing the screw, position and orientation of the at least two localizers are determined and the position at least of the distal tip of the pedicle screw is indicated in a patient model visualized on a monitor using the determined position and orientation of the localizers (step P10).

Afterwards, the sensor carrier, an access needle, a tap and a pedicle screwdriver with another pedicel screw are used for placing the other pedicle screw in one of the neighbouring vertebrae and the at least two pedicle screws placed in the vertebrae are connected with a rod in order to fuse the two neighbouring vertebrae (step P11).

The invention claimed is:

1. A surgical kit, for performing minimally invasive spine surgery, the surgical kit comprising:

a position detection system configured for detecting a position and an orientation of localizers from received sensor signals in a coordinate system;

a sensor carrier configured to be removably arranged in a lumen of a medical instrument, the sensor carrier having at least two localizers, each of the two localizers being configured for providing a sensor signal representing the position and the orientation of the respective localizer; and a plurality of different medical instruments having a lumen in which the sensor carrier can be removably arranged for connecting the respective medical instrument to the position detection system.

2. The surgical kit of claim 1, wherein one of the plurality of medical instruments comprises an access needle having a lumen extending from a distal end of the access needle to a proximal end of the access needle, and wherein the access needle is configured for being guided to a target location in a body of a patient.

3. The surgical kit of claim 2, wherein each of the plurality of different medical instruments comprises at least one of:

(i) a guidewire configured for being inserted into the lumen of the access needle;

(ii) (i) and a guiding rod having a lumen and being configured to be advanced over the guidewire;

(iii) (i) and (ii) and at least one dilation tube configured to be advanced over the guiding rod and for dilating an access path to a target location;

(iv) (i), (ii), (iii), and a working tube configured to be advanced over the at least one dilation tube and for providing a working channel for medical instruments, wherein at its distal end, the working tube is shaped such that it can be anchored to a patient's bone;

(v) (i), (ii), (iii), (iv), and a reamer having a lumen in which an endoscope can be arranged and being configured to be arranged inside the working channel of the working tube for creating a posterior-lateral access to the central nervous system;

(vi) (i), (ii), (iii), (iv), (v), and an endoscope having at least one endoscope working channel for inserting another medical instrument, the endoscope being configured for medical imaging inside a patient's body; and (vii) (i), (ii), (iii), (iv), (v), (vi), and a medical instrument configured to be arranged inside the working channel of the endoscope and for removing at least a part of an intervertebral disc or a surrounding body tissue.

4. The surgical kit of claim 1, wherein each of the plurality of different medical instruments comprises at least one of:

a spine cage configured for restoring disc space between two vertebrae when being arranged between the respective vertebrae;

a lamina screwdriver with lamina screw, the screwdriver having a lumen extending from a proximal end of the screwdriver to a distal end of the lamina screw, the screwdriver being configured for anchoring the lamina screw into a lamina of a vertebra;

a tap for tapping a hole into the vertebra for anchoring a bone screw; and a pedicle screwdriver with a pedicle screw, the screwdriver having a lumen extending from a proximal end of the screwdriver to a distal end of the pedicle screw, the screwdriver being configured for anchoring the pedicle screw into a pedicle of the vertebra.

5. The surgical kit of claim 1, wherein a first one of the localizers is arranged at a distal end of the sensor carrier and a second one of the localizers is arranged at a distance from the first localizer towards a proximal end of the sensor carrier, the sensor carrier further comprising a hypo tube extending from the distal end to the proximal end of the sensor carrier and enclosing the at least two localizers.

6. The surgical kit of claim 5, further comprising a third localizer configured for providing a sensor signal representing a position and an orientation of the third localizer, the third localizer being arranged at a distance from the first and second localizers towards the proximal end of the sensor carrier.

7. The surgical kit of claim 1, further comprising a medical instrument identification setup, the medical instrument identification setup comprising:

a calibration device configured such that its position and orientation in the position detection system's coordinate system can be determined by the position detection system;

a calibration unit configured for calibrating a medical instrument, said medical instrument comprising a tip, with the sensor carrier arranged in its lumen by calculating a distance between the medical instrument's tip and at least one of the two localizers based on the position and orientation of the calibration device and the position and orientation of at least one of the two localizers determined by the position detection system; and a medical instrument identification unit configured for determining a length of the medical instrument's lumen at least from the calculated distance and for using the determined length of the lumen for identifying the medical instrument.

8. The surgical kit of claim 7, wherein the calibration unit is configured for determining a medical instrument's virtual longitudinal axis based on the positions of the at least two localizers.

9. The surgical kit of claim 1, the sensor carrier comprising a proximal and a distal end, wherein the proximal end of the sensor carrier is a distance of between 10 cm and 200 cm from the distal end of the sensor carrier.

10. The surgical kit of claim 9, wherein the proximal end of the sensor carrier is between 15 cm and 150 cm from the distal end of the sensor carrier.

11. The surgical kit of claim 9, wherein the proximal end of the sensor carrier is between 20 cm and 100 cm from the distal end of the sensor carrier.

12. The surgical kit of claim 1, the sensor carrier comprising an outer diameter equal to or smaller than 3 mm.

13. The surgical kit of claim 1, the sensor carrier comprising an outer diameter equal to or smaller than 1.5 mm.

14. The surgical kit of claim 1, the sensor carrier comprising an outer diameter equal to or smaller than 1 mm.

* * * * *